(12) United States Patent
Ohba et al.

(10) Patent No.: US 9,351,920 B2
(45) Date of Patent: May 31, 2016

(54) ORGANOPOLYSILOXANE GRAFT POLYMER

(71) Applicant: KAO CORPORATION, Tokyo (JP)

(72) Inventors: Chihiro Ohba, Wakayama (JP);
Shuichiro Kobaru, Adachi-ku (JP);
Tomoka Maekawa, Sumida-ku (JP);
Satomi Nakazono, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/648,947

(22) PCT Filed: Nov. 5, 2013

(86) PCT No.: PCT/JP2013/079938
§ 371 (c)(1),
(2) Date: Jun. 2, 2015

(87) PCT Pub. No.: WO2014/087779
PCT Pub. Date: Jun. 12, 2014

(65) Prior Publication Data
US 2015/0297498 A1 Oct. 22, 2015

(30) Foreign Application Priority Data
Dec. 3, 2012 (JP) .................................. 2012-264598

(51) Int. Cl.
| | |
|---|---|
| A61K 8/89 | (2006.01) |
| C08G 77/442 | (2006.01) |
| C08G 77/388 | (2006.01) |
| A61Q 5/06 | (2006.01) |
| A61K 8/895 | (2006.01) |
| C08F 283/12 | (2006.01) |
| C08G 77/42 | (2006.01) |
| C08F 226/06 | (2006.01) |
| C08F 220/34 | (2006.01) |

(52) U.S. Cl.
CPC . *A61K 8/89* (2013.01); *A61K 8/895* (2013.01); *A61Q 5/06* (2013.01); *C08F 283/12* (2013.01); *C08G 77/388* (2013.01); *C08G 77/42* (2013.01); *C08G 77/442* (2013.01); *C08F 220/34* (2013.01); *C08F 226/06* (2013.01)

(58) Field of Classification Search
None
See application file for complete search history.

(56) References Cited

U.S. PATENT DOCUMENTS

| | | | |
|---|---|---|---|
| 4,985,155 A | 1/1991 | Yamada et al. | |
| 5,468,477 A | 11/1995 | Kumar et al. | |
| 6,007,800 A | 12/1999 | Dubief et al. | |
| 6,011,126 A | 1/2000 | Dubief et al. | |
| 6,201,093 B1 | 3/2001 | Messner et al. | |
| 6,350,439 B1 | 2/2002 | Dupuis | |
| 6,403,074 B1 | 6/2002 | Blankenburg et al. | |
| 6,627,696 B1 | 9/2003 | Takao et al. | |
| 7,341,674 B1* | 3/2008 | Trinh .................... | D06M 15/19 106/15.05 |
| 2003/0199642 A1 | 10/2003 | Schneider et al. | |
| 2005/0027283 A1* | 2/2005 | Richard ............... | A61K 9/0024 604/890.1 |
| 2006/0217285 A1 | 9/2006 | Destarac | |
| 2010/0297041 A1 | 11/2010 | Smith et al. | |
| 2012/0216823 A1 | 8/2012 | Fukuhara et al. | |

FOREIGN PATENT DOCUMENTS

| | | |
|---|---|---|
| EP | 2865693 A1 | 4/2015 |
| JP | 1-239175 A | 9/1989 |
| JP | 6-92825 A | 4/1994 |
| JP | 9-110633 A | 4/1997 |
| JP | 10-511988 A | 11/1998 |
| JP | 10-512233 A | 11/1998 |
| JP | 11-500746 A | 1/1999 |
| JP | 11-269269 A | 10/1999 |
| JP | 2000-355523 A | 12/2000 |
| JP | 2001-81018 A | 3/2001 |
| JP | 2004-506669 A | 3/2004 |
| JP | 2006-505686 A | 2/2006 |
| JP | 2006-272320 A | 10/2006 |
| JP | 2008-127526 A | 6/2008 |
| JP | 2011-504185 A | 2/2011 |
| WO | WO 2011/062210 A1 | 5/2011 |

OTHER PUBLICATIONS

International Search Report, issued in PCT/JP2013/079938, dated Feb. 4, 2014.
European Patent Office Communication and extended search report issued in the corresponding European Patent Application No. 13860596.9 on Apr. 4, 2016.

* cited by examiner

*Primary Examiner* — Marc Zimmer
(74) *Attorney, Agent, or Firm* — Birch, Stewart, Kolasch & Birch, LLP

(57) ABSTRACT

The present invention relates to an organopolysiloxane graft polymer including an organopolysiloxane segment as a main chain thereof and an unsaturated monomer-derived polymer segment as a side chain thereof, in which a content of the organopolysiloxane segment in the organopolysiloxane graft polymer is not less than 35% by mass and not more than 70% by mass, and the unsaturated monomer-derived polymer segment contains a repeating unit derived from a nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from a cationic unsaturated monomer in an amount of not less than 10% by mass and not more than 60% by mass.

18 Claims, No Drawings

ORGANOPOLYSILOXANE GRAFT POLYMER

FIELD OF THE INVENTION

The present invention relates to an organopolysiloxane graft polymer, and more particularly, to an organopolysiloxane graft polymer that is useful as a hair cosmetic.

BACKGROUND OF THE INVENTION

Organopolysiloxanes have various excellent characteristics. Therefore, the organopolysiloxanes having various structures are compounded in shampoos, hair conditioners, etc., and have been used as a touch improver or the like.

For example, Patent Literature 1 aims at providing a hairdressing method that is capable of imparting a soft touch and a natural finish feeling to hair, firmly fixing a hair style, maintaining the hair style for a long period of time without change even when exposed to external factors (such as combing of hand or fingers through hair, wind, vibrations, etc.), and further hairdressing the hair again, and discloses a hair cosmetic containing a poly(N-acyl alkylene imine)-modified organopolysiloxane. In the invention of Patent Literature 1, there is described such a hairdressing method including the steps of applying the hair cosmetic containing a poly(N-acyl alkylene imine)-modified organopolysiloxane to hair, shaping the hair at a hair temperature of 50° C. or higher, and then cooling the hair to a temperature of lower than 50° C. to fix a style of the hair thus shaped.

In addition, Patent Literature 2 discloses a cosmetic composition containing an organopolysiloxane graft polymer produced by subjecting a mercapto-modified silicone and a radical-polymerizable vinyl monomer to solution polymerization. Patent Literature 3 discloses a hair cosmetic containing an organopolysiloxane graft polymer.

CITATION LIST

Patent Literature

Patent Literature 1: WO 2011/062210A
Patent Literature 2: JP 10-512233A
Patent Literature 3: JP 6-92825A

SUMMARY OF THE INVENTION

The present invention relates to an organopolysiloxane graft polymer including an organopolysiloxane segment as a main chain thereof and an unsaturated monomer-derived polymer segment as a side chain thereof, in which a content of the organopolysiloxane segment in the organopolysiloxane graft polymer is not less than 35% by mass and not more than 70% by mass, and the unsaturated monomer-derived polymer segment contains a repeating unit derived from a nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from a cationic unsaturated monomer in an amount of not less than 10% by mass and not more than 60% by mass.

DETAILED DESCRIPTION OF THE INVENTION

Patent Literature 1 describes that a weight ratio of an organopolysiloxane segment in the poly(N-acyl alkylene imine)-modified organopolysiloxane is preferably in the range of from 35 to 65% by weight from the viewpoints of various performances such as a solubility or dispersibility in a solvent, facilitated hair shaping upon hairdressing and a touch feeling of a hair after hairdressing. The poly(N-acyl alkylene imine)-modified organopolysiloxane described in Patent Literature 1 is produced by first subjecting a cyclic imino ether to living polymerization to obtain an end-reactive poly(N-acyl alkylene imine) and then connecting an organopolysiloxane segment (e.g., an amino-modified silicone) to the end-reactive poly(N-acyl alkylene imine). However, the living polymerization step and the connecting step require dehydration for removal of a solvent or the like, and water or an alcohol solvent such as ethanol, etc., which can be compounded in a hair cosmetic, is unusable as a polymerization solvent in these steps. Therefore, since it is required to remove the polymerization solvent by drying, etc., there is a large burden on production of the above organopolysiloxane.

In addition, a weight ratio of an organopolysiloxane segment in any of the organopolysiloxane graft polymers described in Examples of Patent Literature 2 is as low as 30% by weight. Therefore, it is suggested that these organopolysiloxane graft polymers fail to satisfy the requirements of the hairdressing method described in Patent Literature 1.

Further, in Example 4 of Patent Literature 3, there is disclosed the organopolysiloxane graft polymer produced using a radical-polymerizable vinyl monomer containing a cationic group. However, a weight ratio of an organopolysiloxane segment in the organopolysiloxane graft polymer is as low as 15% by weight. Therefore, it is also suggested that the organopolysiloxane graft polymer fails to satisfy the requirements of the hairdressing method described in Patent Literature 1.

The present invention relates to a cationic group-containing organopolysiloxane compound that is optimum for use in a hairdressing method including the steps of shaping hair at a hair temperature of 50° C. or higher and then cooling the hair to a temperature of lower than 50° C. to fix a style of the hair thus shaped, and can exhibit an excellent hair set retentivity under high humidity conditions.

The present inventors have been found that when using an organopolysiloxane graft polymer having a specific structure, it is possible to provide a hairdressing method including the steps of shaping hair at a hair temperature of 50° C. or higher and then cooling the hair to a temperature of lower than 50° C. to fix a style of the hair thus shaped. In addition, the inventors have also found that the aforementioned organopolysiloxane graft polymer can exhibit an excellent hair set retentivity under high humidity conditions.

The present invention relates to an organopolysiloxane graft polymer, a process for producing the organopolysiloxane graft polymer, a use of the organopolysiloxane graft polymer for a hair cosmetic, a hair cosmetic and a hairdressing method, as described below.

[1] An organopolysiloxane graft polymer including an organopolysiloxane segment as a main chain thereof and an unsaturated monomer-derived polymer segment as a side chain thereof, in which a content of the organopolysiloxane segment in the organopolysiloxane graft polymer is not less than 35% by mass and not more than 70% by mass, and the unsaturated monomer-derived polymer segment contains a repeating unit derived from a nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from a cationic unsaturated monomer in an amount of not less than 10% by mass and not more than 60% by mass.

[2] A process for producing an organopolysiloxane graft polymer including an organopolysiloxane segment as a main chain thereof and an unsaturated monomer-derived polymer segment as a side chain thereof, said process including the step of polymerizing unsaturated monomers including a nonionic unsaturated monomer having a glass transition temperature Tg of 60° C. or higher and a cationic unsaturated monomer in the presence of a radical-reactive organopolysiloxane represented by the following general formula (5) or (6), in which a content of the organopolysiloxane segment in the organopolysiloxane graft polymer is not less than 35% by mass and not more than 70% by mass, and the unsaturated monomer-derived polymer segment contains a repeating unit derived from the nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from the cationic unsaturated monomer in an amount of not less than 10% by mass and not more than 60% by mass:

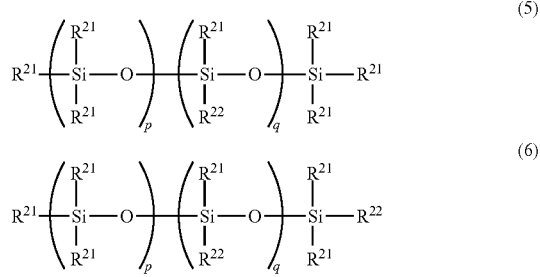

wherein $R^{21}$ groups are each independently an alkyl group having not less than 1 and not more than 22 carbon atoms or an aryl group having not less than 6 and not more than 14 carbon atoms; $R^{22}$ is an alkyl group containing a radical-reactive functional group; p is a number of not less than 2 and not more than 4,000; and q is a number of not less than 2 and not more than 500, in which repeating units in number of p and repeating units in number of q may be bonded to each other either in a block form or in a random form.

[3] A hair cosmetic including the organopolysiloxane graft polymer according to the above [1].

[4] A use of the organopolysiloxane graft polymer according to the above [1] for a hair cosmetic.

[5] A hairdressing method including the step of applying the organopolysiloxane graft polymer according to the above [1] to hair.

The organopolysiloxane graft polymer of the present invention is optimum for use in a hairdressing method including the steps of shaping hair at a hair temperature of 50° C. or higher and then cooling the hair to a temperature of lower than 50° C. to fix a style of the hair thus shaped, and can exhibit an excellent hair set retentivity under high humidity conditions.

[Organopolysiloxane Graft Polymer]

The organopolysiloxane graft polymer according to the present invention (hereinafter also referred to merely as a "graft polymer of the present invention") includes an organopolysiloxane segment as a main chain thereof and an unsaturated monomer-derived polymer segment as a side chain thereof, in which a content of the organopolysiloxane segment in the organopolysiloxane graft polymer is not less than 35% by mass and not more than 70% by mass, and the unsaturated monomer-derived polymer segment contains a repeating unit derived from a nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from a cationic unsaturated monomer in an amount of not less than 10% by mass and not more than 60% by mass.

In the graft polymer of the present invention, it is preferred that two or more side chains are respectively bonded to an optional silicon atom in the organopolysiloxane segment constituting the main chain of the graft polymer through an alkylene group containing a hetero atom, and it is more preferred that the two or more side chains are respectively bonded to one or more silicon atoms except for those silicon atoms bonded to both ends of the organopolysiloxane segment through the alkylene group, and it is still more preferred that the two or more side chains are respectively bonded to two or more silicon atoms except for those silicon atoms bonded to both ends of the organopolysiloxane segment through the alkylene group.

<Organopolysiloxane Segment>

The graft polymer of the present invention contains the organopolysiloxane segment as a main chain thereof.

The chemical structure of the organopolysiloxane segment is not particularly limited. Specific Examples of the preferred organopolysiloxane segment include modified organopolysiloxane segments represented by the following general formula (1) or (2).

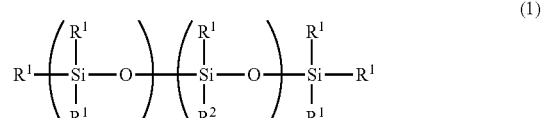

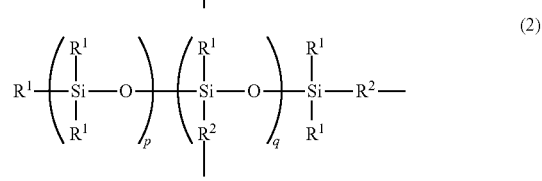

In the above formulae (1) and (2), $R^1$ groups are each independently an alkyl group having not less than 1 and not more than 22 carbon atoms or an aryl group having not less than 6 and not more than 14 carbon atoms; and $R^2$ groups are each an alkylene group that may contain a hetero atom. Also, p is a number of not less than 2 and not more than 4,000, and q is a number of not less than 2 and not more than 500. In the general formulae (1) and (2), the repeating units in the number of p and the repeating units in the number of q may be bonded to each other either in a block form or in a random form.

In the above general formulae (1) and (2), the alkyl group represented by $R^1$ is a straight-chain alkyl group, a branched-chain alkyl group or a cyclic alkyl group. The number of carbon atoms of the alkyl group represented by $R^1$ is preferably not less than 1 and not more than 10, and more preferably not more than 6, from the viewpoint of improving a formulation stability of the graft polymer of the present invention when compounded in a hair cosmetic (hereinafter also referred to as a "water dispersibility of the graft polymer of the present invention"). Specific examples of the alkyl group represented by $R^1$ include a methyl group, an ethyl group, an n-propyl group, an isopropyl group, an n-butyl group, a tert-butyl group, a pentyl group, a hexyl group, a cyclohexyl group, a heptyl group, an octyl group, a nonyl group, a decyl group, an undecyl group, a dodecyl group, an octadecyl group, a nonadecyl group, an eicosyl group and a docosyl group.

The number of carbon atoms of the aryl group represented by $R^1$ is preferably not less than 6 and not more than 12, and more preferably not more than 9, from the viewpoint of a good water dispersibility of the graft polymer of the present invention. Specific examples of the aryl group represented by $R^1$ include a phenyl group, a tolyl group, a xylyl group, a naphthyl group, a biphenyl group, an anthryl group and a phenanthryl group.

Of these groups as $R^1$, from the viewpoint of a good water dispersibility of the graft polymer of the present invention, preferred are straight-chain or branched-chain alkyl groups having 1 to 6 carbon atoms, more preferred are straight-chain or branched-chain alkyl groups having 1 to 3 carbon atoms, and still more preferred is a methyl group.

In the above general formulae (1) and (2), p is a number of not less than 2 and not more than 4,000, and q is a number of not less than 2 and not more than 500. From the viewpoint of a good touch feeling of hair after setting the hair with a hair cosmetic including the organopolysiloxane graft polymer of the present invention (hereinafter also referred to as a "hair cosmetic of the present invention"), p is preferably a number of not less than 50, more preferably not less than 100, and still more preferably not less than 150, and is also preferably a number of not more than 2,000, more preferably not more than 1,500, and still more preferably not more than 1,000. From the viewpoint of a good water dispersibility of the graft polymer of the present invention, q is preferably a number of not less than 3, and more preferably not less than 5, and from the viewpoints of a good hair settability of the hair cosmetic of the present invention, q is also preferably a number of not more than 50, and more preferably not more than 30.

In the above general formulae (1) and (2), a part or whole of the alkylene group ($R^2$) which may contain a hetero atom functions as a connecting group between the main chain and the unsaturated monomer-derived polymer segment as the side chain. In the case where any alkylene group that may contain a hetero atom is present in the form of a group unbonded to the unsaturated monomer-derived copolymer segment, the alkylene group that may contain a hetero atom is bonded to the main chain and a hydrogen atom.

In the present invention, the number of carbon atoms of the alkylene group that may contain a hetero atom is preferably not less than 2, and more preferably not less than 3, from the viewpoint of a good availability of the raw materials used upon production of the graft polymer of the present invention. Also, from the viewpoint of a good water dispersibility of the graft polymer of the present invention, the number of carbon atoms of the alkylene group that may contain a hetero atom is preferably not more than 20, more preferably not more than 15, still more preferably not more than 10, and even still more preferably not more than 8.

In the present invention, the alkylene group that may contain a hetero atom may be interrupted by at least one atom or functional group selected from the group consisting of an oxygen atom, a sulfur atom, —NH—, —COO—, —NHCO— and —NR³CO—. That is, the alkylene group that may contain a hetero atom may have a structure constituted of "-(an alkylene group portion 1)-(the above atom or functional group)-(an alkylene group portion 2)-". In this case, the number of carbon atoms of the alkylene group that may contain a hetero atom means a sum of the number of carbon atoms of the alkylene group portion 1 and the number of carbon atoms of the alkylene group portion 2. In the above —NR³CO—, $R^3$ is an alkyl group having not less than 1 and not more than 3 carbon atoms. When the alkylene group that may contain a hetero atom is interrupted by the above atom or functional group, from the viewpoint of facilitated production of the graft polymer of the present invention, the alkylene group that may contain a hetero atom is preferably interrupted by —NHCO—.

In the present invention, the alkylene group that may contain a hetero atom may be substituted with at least one monovalent group selected from the group consisting of a hydroxy group, an amino group, a ($C_1$-$C_3$)alkyl amino group, a di-($C_1$-$C_3$)alkyl amino group, an amide group obtained by dehydration condensation of an amino group and a fatty acid having 2 to 4 carbon atoms, a carboxy group, and a ($C_1$-$C_3$) alkyl ester group. In this case, the number of carbon atoms of the alkylene group that may contain a hetero atom does not include the number of carbon atoms contained in the above substituent group. From the viewpoint of a good availability of the raw materials upon production of the graft polymer of the present invention, the alkylene group that may contain a hetero atom is preferably substituted with at least one monovalent group selected from the group consisting of an acetamide group, a ($C_1$-$C_3$)alkyl amino group and an amine group.

In the present invention, the alkylene group that may contain a hetero atom may be substituted with a divalent hetero atom or a divalent group containing a hetero atom selected from the group consisting of —O—, —S—, —NH—, —NR¹⁴— and —COO—, in which $R^{14}$ is a ($C_1$-$C_3$)alkyl group that may be substituted with a dimethyl amino group. The divalent hetero atom or the divalent group containing a hetero atom is bonded to the unsaturated monomer-derived polymer segment when the alkylene group that may contain a hetero atom functions as a connecting group to the unsaturated monomer-derived polymer segment, and in otherwise cases, the divalent hetero atom or the divalent group containing a hetero atom is bonded to a hydrogen atom.

From the viewpoint of facilitated production of the graft polymer of the present invention, the alkylene group that may contain a hetero atom is preferably substituted with —S—.

The alkylene group ($R^2$) which may contain a hetero atom is preferably bonded to the unsaturated monomer-derived polymer segment through the hetero atom, more preferably through a nitrogen atom, an oxygen atom or a sulfur atom, and still more preferably through a sulfur atom.

Therefore, the "alkylene group that may contain a hetero atom" represented by $R^2$ corresponds to (i) an unsubstituted alkylene group; (ii) an alkylene group interrupted by at least one atom or functional group selected from the group consisting of an oxygen atom, a sulfur atom, —NH—, —COO—, —NHCO— and —NR³CO—; (iii) an alkylene group substituted with at least one group selected from the group consisting of a hydroxy group, an amino group, a ($C_1$-$C_3$)alkyl amino group, a di-($C_1$-$C_3$)alkyl amino group, an amide group obtained by dehydration condensation of an amino group and a fatty acid having 2 to 4 carbon atoms, a carboxy group, and a ($C_1$-$C_3$)alkyl ester group; (iv) an alkylene group substituted with a divalent hetero atom or a divalent group containing a hetero atom selected from the group consisting of —O—, —S—, —NH—, —NR¹⁴—, and —COO—; and an alkylene group in the form of a combination of any two or more of the above (ii), (iii) and (iv).

Specific examples of the alkylene group that may contain a hetero atom as used in the present invention include those group represented by the following formulae (i) to (xii). Of these groups, from the viewpoint of facilitated production of the graft polymer of the present invention, preferred are those groups represented by the following formulae (xi) and (xii), and more preferred is the group represented by the following formula (xii).

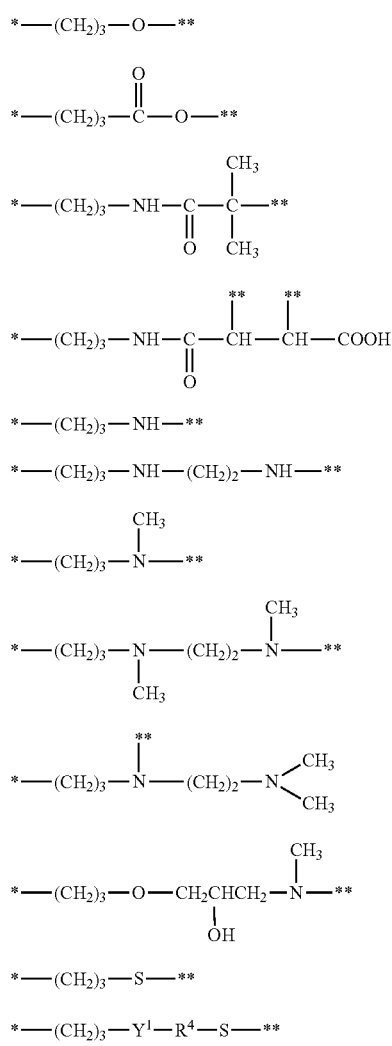

In the formulae (i) to (xii), "*" represents a moiety bonded to the silicon atom in the general formula (1), whereas "**" represents a moiety bonded to the unsaturated monomer-derived polymer segment.

In the formula (xii), $Y^1$ is at least one group selected from the group consisting of —O—, —OCO—, —COO—, —CONH— and —NHCO—. Of these groups, from the viewpoint of facilitated production of the graft polymer of the present invention, preferred is —CONH— or —NHCO—, and more preferred is —NHCO—.

Also, in the formula (xii), $R^4$ is an alkylene group that may be substituted with at least one monovalent group selected from the group consisting of a hydroxy group, an amino group, a $(C_1$-$C_3)$alkyl amino group, a di-$(C_1$-$C_3)$alkyl amino group, an amide group obtained by dehydration condensation of an amino group and a fatty acid having 2 to 4 carbon atoms, a carboxy group, and a $(C_1$-$C_3)$alkyl ester group. Of these substituent groups that may be bonded to the alkylene group as $R^4$, from the viewpoint of a good availability of the raw materials upon production of the graft polymer, preferred are an acetamide group, a $(C_1$-$C_3)$alkyl amino group and an amino group. The number of carbon atoms of the alkylene group represented by $R^4$ is preferably not less than 2, and more preferably not less than 3, from the viewpoint of facilitated production of the graft polymer of the present invention, and is also preferably not more than 15, more preferably not more than 10, and still more preferably not more than 6, from the viewpoint of a good water dispersibility of the graft polymer of the present invention.

Specific examples of $R^4$ include those groups represented by the following formulae (xiii) to (xv).

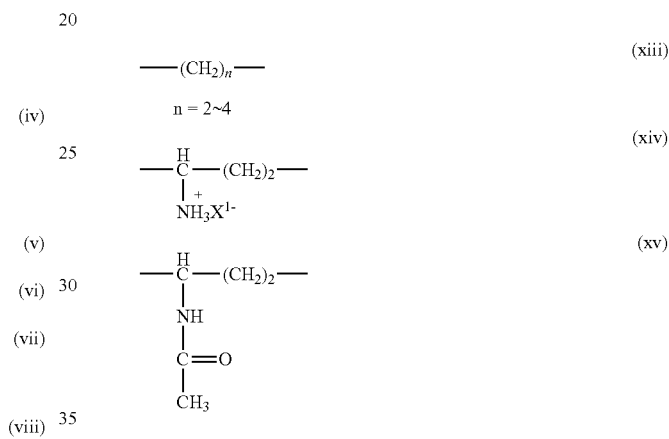

In the formula (xiv), $X^{1-}$ represents an anion selected from the group consisting of a halide ion such as a chloride ion and a bromide ion, an acetate ion and an alkyl sulfate ion having not less than 1 and not more than 3 carbon atoms.

<Unsaturated Monomer-Derived Polymer Segment>
<Repeating Unit Derived from Nonionic Unsaturated Monomer Having Tg of 60° C. or Higher>

The organopolysiloxane graft polymer of the present invention contains an unsaturated monomer-derived polymer segment as a side chain thereof. From the viewpoint of a good hair set retentivity under high humidity conditions upon setting the hair using the hair cosmetic of the present invention, the unsaturated monomer-derived polymer segment contains a repeating unit derived from a nonionic unsaturated monomer having Tg of 60° C. or higher (except for a repeating unit derived from an unsaturated monomer containing an amino group) in an amount of not less than 40% by mass, preferably not less than 45% by mass, and more preferably not less than 50% by mass. Also, from the viewpoint of a good touch feeling of hair after hair setting upon setting the hair using the hair cosmetic of the present invention, the unsaturated monomer-derived polymer segment contains the repeating unit derived from a nonionic unsaturated monomer having Tg of 60° C. or higher in an amount of not more than 90% by mass, preferably not more than 85% by mass, and more preferably not more than 80% by mass.

Meanwhile, the repeating unit derived from an unsaturated monomer containing an amino group may be protonated depending upon environmental conditions during production of the products or upon use thereof, and as a result, converted into a repeating unit other than the repeating unit derived from a nonionic unsaturated monomer. Therefore, in the present invention, the repeating unit derived from an unsaturated monomer containing an amino group is excluded from the "repeating unit derived from a nonionic unsaturated monomer".

From the viewpoint of a good hair settability and a good hair set retentivity under high humidity conditions upon setting the hair using the hair cosmetic of the present invention, Tg of the nonionic monomer is preferably not lower than 80° C., more preferably not lower than 100° C., and still more preferably not lower than 110° C., and is also preferably not higher than 190° C., more preferably not higher than 170° C., and still more preferably not higher than 150° C.

Tg of the unsaturated monomer as used in the present invention means Tg of a homopolymer obtained by polymerizing the monomer. Also, in the present invention, the nonionic unsaturated monomer having Tg of 60° C. or higher means an unsaturated monomer having Tg of 60° C. or higher as described in "Polymer Handbook", 4th Edition, Vol. 1, VI/193-VI/277, Wiley-Interscience. In addition, the repeating unit derived from an unsaturated monomer as used in the present invention means a repeating unit in a homopolymer obtained by polymerizing the unsaturated monomer.

Specific examples of the nonionic unsaturated monomer having Tg of 60° C. or higher (except for an unsaturated monomer containing an amino group) include an acrylate compound, an acrylamide compound, a methacrylate compound, a methacrylamide compound and a styrene compound.

Specific examples of the acrylate compound include adamantyl acrylate, 4-biphenylyl acrylate, tert-butyl acrylate, 2-tert-butylphenyl acrylate, 4-tert-butylphenyl acrylate, 3,5-dimethyl adamantyl acrylate, ferrocenyl ethyl acrylate, ferrocenyl methyl acrylate, 2,2,2-trifluoroethyl α-fluoroacrylate, 2,2,3,3-tetrafluoropropyl α-fluoroacrylate, 2,2,3,3,3-heptafluoropropyl α-fluoroacrylate, isobornyl acrylate, 4-methoxycarbonylphenyl acrylate, 2-naphthyl acrylate, pentabromobenzyl acrylate and pentachlorobenzyl acrylate.

Specific examples of the acrylamide compound include acrylamide, N-sec-butyl acrylamide, N-tert-butyl acrylamide, N,N-diisopropyl acrylamide, N,N-dimethyl acrylamide, isohexyl acrylamide, isooctyl acrylamide, N-(1-methylbutyl) acrylamide, N-methyl-N-phenyl acrylamide and N-(4-piperidyl) acrylamide.

Specific examples of the methacrylate compound include adamantyl methacrylate, 4-tert-butylcyclohexyl methacrylate, sec-butyl methacrylate, tert-butyl methacrylate, 4-tert-butylphenyl methacrylate, 2-chloroethyl methacrylate, 2-cyanoethyl methacrylate, 4-cyanomethylphenyl methacrylate, 4-cyanophenyl methacrylate, cyclobutyl methacrylate, cyclohexyl methacrylate, cyclooctyl methacrylate, cyclopentyl methacrylate, 2-decahydronaphthyl methacrylate, 3,5-dimethyl adamantyl methacrylate, 3,3-dimethyl-2-butyl methacrylate, ethyl methacrylate, ferrocenylethyl methacrylate, ferrpcenylmethyl methacrylate, 2,2,2-trifluoroethyl methacrylate, 2,2,3,3-tetrafluoropropyl methacrylate, 2,2,3,3,3-heptafluoropropyl methacrylate, glycidyl methacrylate, 2-hydroxypropyl methacrylate, 2-hydroxyethyl methacrylate, isobornyl methacrylate, isopropyl methacrylate, 4-methoxycarbonylphenyl methacrylate, methyl methacrylate, phenyl methacrylate, 1,1,1-trifluoro-2-propyl methacrylate, 3,3,5-trimethylcyclohexyl methacrylate, trimethylsilyl methacrylate, 2,3-xylenyl methacrylate and 2,6-xylenyl methacrylate.

Specific examples of the methacrylamide compound include 4-butoxycarbonylphenyl methacrylamide, N-tert-butyl methacrylamide, N-carboxyphenyl methacrylamide, 4-ethoxycarbonylphenyl methacrylarnide and 4-methoxycarbonylphenyl methacrylamide.

Specific examples of the styrene compound include 4-acetyl styrene, 4-p-anisoyl styrene, 4-benzoyl styrene, (2-benzoyloxymethyl)styrene, 3-(4-biphenylyl)styrene, 4-(4-biphenylyl)styrene, 5-bromo-2-ethoxystyrene, 5-bromo-2-methoxystyrene, 4-bromostyrene, 2-butoxycarbonyl styrene, 4-butoxycarbonyl styrene, 2-butoxymethyl styrene, 5-tert-butyl-2-methyl styrene, 4-sec-butyl styrene, tert-butyl styrene, 4-tert-butyl styrene, 4-butyryl styrene, 2-carboxystyrene, 4-carboxystyrene, 4-chloro-3-fluorostyrene, 4-chloro-2-methyl styrene, 4-chloro-3-methyl styrene, 2-chlorostyrene, 3-chlorostyrene, 4-chlorostyrene, 4-cyanostyrene, 2,4-dichlorostyrene, 2,5-dichlorostyrene, 2,6-dichlorostyrene, 3,4-dichlorostyrene, 2,5-fluorostyrene, 2,4-diisopropyl styrene, 2,5-diisopropyl styrene, 2,4-dimethyl styrene, 2,5-dimethyl styrene, 3,4-dimethyl styrene, 3,5-dimethyl styrene, 2-ethoxycarbonyl styrene, 4-ethoxycarbonyl styrene, 2-ethoxymethyl styrene, 4-ethoxystyrene, 2-ethyl styrene, 2-fluoro-5-methyl styrene, 4-fluorostyrene, 4-hexanoyl styrene, 4-hexanoylcarbonyl styrene, 2-hydroxymethyl styrene, 4-hydroxystyrene, 2-isobutoxycarbonyl styrene, 4-isobutoxycarbonyl styrene, 2-isopentyloxycarbonyl styrene, 2-isopentyloxymethyl styrene, 2-methoxycarbonyl styrene, 4-methoxycarbonyl styrene, 2-methoxymethyl styrene, 4-methoxymethyl styrene, 4-methoxy-2-methyl styrene, 2-methoxystyrene, 4-methoxystyrene, 2-methyl styrene, 3-methyl styrene, 4-methyl styrene, 2,3,4,5,6-pentafluorostyrene, 2-pentyloxycarbonyl styrene, perfluorostyrene, 2-phenoxycarbonyl styrene, 4-phenoxystyrene, 4-phenylacetyl styrene, 4-phenyl styrene, styrene, 2,4,5-trimethyl styrene, 2,4,6-trimethyl styrene, neopentyloxyethylene and methoxyethylene.

Examples of the nonionic unsaturated monomer other than the aforementioned compounds include adamantyl crotonate, adamantyl sorbate, 3,5-dimethyl adamantyl crotonate, 4-vinyl phenol, N-carbazoyl ethylene, ferrocenyl ethylene, phthalimide ethylene, 4-pyridyl ethylene and N-vinyl pyrrolidone.

Of these nonionic unsaturated monomers, from the viewpoint of a good hair settability and a good hair set retentivity under high humidity conditions upon setting the hair using the hair cosmetic of the present invention, preferred is at least one nonionic unsaturated monomer selected from the group consisting of tert-butyl acrylate, acrylamide, N-sec-butyl acrylamide, N-tert-butyl acrylamide, N,N-dibutyl acrylamide, N,N-diisopropyl acrylamide, N,N-dimethyl acrylamide, isohexyl acrylamide, isooctyl acrylamide, N-(1-methylbutyl)acrylamide, sec-butyl methacrylate, tert-butyl methacrylate and N-tert-butyl methacrylamide; more preferred is at least one nonionic unsaturated monomer selected from the group consisting of tert-butyl acrylate, N-tert-butyl acrylamide, tert-butyl methacrylate and N-tert-butyl methacrylamide; and still more preferred is N-tert-butyl acrylamide.

The repeating unit derived from the nonionic unsaturated monomer having Tg of 60° C. or higher may be used alone or in the form of a mixture of any two or more kinds thereof.

(Repeating Unit Derived from Cationic Unsaturated Monomer)

The unsaturated monomer-derived polymer segment as a side chain of the organopolysiloxane graft polymer of the present invention contains not only the repeating unit derived from the aforementioned nonionic unsaturated monomer having Tg of 60° C. or higher, but also a repeating unit derived from a cationic unsaturated monomer, from the viewpoints of a good hair settability upon setting the hair using the hair cosmetic of the present invention and facilitated removal of the organopolysiloxane graft polymer of the present invention upon shampooing (hereinafter also referred to as "washability"). The content of the repeating unit derived from the cationic unsaturated monomer in the unsaturated monomer-derived polymer segment is not less than 10% by mass, preferably not less than 15% by mass, and more preferably not less than 20% by mass. Also, from the viewpoint of a good hair settability upon setting the hair using the hair cosmetic of the present invention, the content of the repeating unit derived from the cationic unsaturated monomer in the unsaturated monomer-derived polymer segment is not more than 60% by mass, preferably not more than 55% by mass, and more preferably not more than 50% by mass.

The cationic unsaturated monomer as used in the present invention means an unsaturated monomer containing a cationic functional group, and the cationic functional group means not only a functional group having a positive charge irrespective of environmental conditions, such as a quaternary ammonium group and a pyridinium group, but also a functional group capable of being protonated depending upon environmental conditions to have a positive charge thereon, such as a primary, secondary or tertiary amino group and a pyridino group.

From the viewpoints of a good hair settability upon setting the hair using the hair cosmetic of the present invention and a good washability, the cationic unsaturated monomer is preferably a compound represented by the following general formula (3):

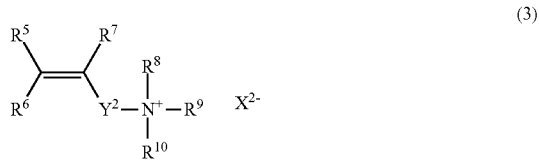

In the general formula (3), $R^5$, $R^6$ and $R^7$ are each independently a hydrogen atom or a methyl group; and $R^8$, $R^9$ and $R^{10}$ are each independently a hydrogen atom or an alkyl group having 1 to 3 carbon atoms. From the viewpoint of a good availability of the raw materials upon production of the organopolysiloxane graft polymer of the present invention, $R^5$ and $R^6$ are each preferably a hydrogen atom. Also, from the viewpoint of a good availability of the raw materials upon production of the organopolysiloxane graft polymer of the present invention, $R^8$ and $R^9$ are each preferably a methyl group or an ethyl group. In addition, from the viewpoint of a good availability of raw materials upon production of the organopolysiloxane graft polymer of the present invention, $R^{10}$ is preferably a hydrogen atom. $Y^2$ is a group selected from the group consisting of an alkylene group having 1 to 12 carbon atoms, —COOR$^{11}$—, —CONHR$^{11}$—, —OCOR$^{11}$— and —R$^{12}$—OCO—R$^{11}$— wherein R$^{11}$ and R$^{12}$ are each independently an alkylene group having 1 to 5 carbon atoms. From the viewpoint of a good availability of the raw materials upon production of the organopolysiloxane graft polymer of the present invention, R$^{11}$ is preferably an alkylene group having 2 to 3 carbon atoms, and R$^{12}$ is preferably a methylene group. Also, from the viewpoint of a good availability of the raw materials upon production of the organopolysiloxane graft polymer of the present invention, $Y^2$ is preferably —COOR$^{11}$— or —CONHR$^{11}$—.

$X^{2-}$ represents an anion. Examples of the anion include a halide ion such as a chloride ion and a bromide ion; and an organic acid ion such as an alkylsulfuric acid ion having not less than 1 and not more than 3 carbon atoms, an acetic acid ion, a lactic acid ion, a benzoic acid ion, an adipic acid ion, a formic acid ion, a malic acid ion and a glycolic acid ion. Of these anions, from the viewpoints of a good touch feeling of hair after hair setting and a good hair set retentivity under high humidity conditions when setting the hair with a hair cosmetic using the organopolysiloxane graft polymer of the present invention, preferred are an alkylsulfuric acid ion having not less than 1 and not more than 3 carbon atoms, a lactic acid ion, a formic acid ion, a malic acid ion and a glycolic acid ion, and more preferred is a lactic acid ion.

Meanwhile, in the case where the side chain of the organopolysiloxane graft polymer of the present invention contains a repeating unit derived from the cationic unsaturated monomer having a structure represented by the general formula (3) in which at least one of $R^8$ to $R^{10}$ is a hydrogen atom, the repeating unit may be deprotonated and converted into a repeating unit derived from a nonionic unsaturated monomer under specific conditions. In the present invention, even if the nonionic unsaturated monomer thus produced has Tg of 60° C. or higher, the repeating unit derived from such a monomer is regarded not as the repeating unit derived from the nonionic unsaturated monomer having Tg of 60° C. or higher, but as the repeating unit derived from the cationic unsaturated monomer.

In addition, in the case where the side chain of the organopolysiloxane graft polymer of the present invention contains the repeating unit derived from the cationic unsaturated monomer having a structure represented by the general formula (3) in which at least one of $R^8$ to $R^{10}$ is a hydrogen atom, the repeating unit may be partially deprotonated.

Specific examples of the cationic unsaturated monomer used in the present invention include dimethylaminoethyl (meth)acrylate, diethylaminoethyl(meth)acrylate, dimethylaminopropyl(meth)acrylate, diethylaminopropyl(meth)acrylate, dimethylaminoethyl(meth)acrylamide, diethylaminoethyl(meth)acrylamide, dimethylaminopropyl(meth)acrylamide, diethylaminopropyl(meth)acrylamide, 2-vinyl pyridine, 4-vinyl pyridine and compounds having a structure obtained by neutralizing the above respective compounds with an acid represented by H$^+$X$^{2-}$ in which X$^{2-}$ is the same as $X^{2-}$ in the above general formula (3). Further examples of the cationic unsaturated monomer include compounds whose counter ion is X$^{2-}$, such as (meth)acryloyloxyethyl trimethyl ammonium, (meth)acryloyloxypropyl trimethyl ammonium, (meth)acryloylaminoethyl trimethyl ammonium, (meth)acryloylaminopropyl trimethyl ammonium, diallyl dimethyl ammonium, 1-ethyl-4-vinyl pyridinium and 1,2-dimethyl-5-vinyl pyridinium.

Of these cationic unsaturated monomers, preferred are dimethylaminopropyl(meth)acrylamide and diethylaminoethyl(meth)acrylamide.

(Repeating Unit Derived from Other Unsaturated Monomers)

In the organopolysiloxane graft polymer of the present invention, the polymer derived from the unsaturated monomer as a side chain thereof may further contain one or more repeating units derived from an unsaturated monomer other than the nonionic unsaturated monomer having Tg of 60° C. or higher and the cationic unsaturated monomer. The repeating unit derived from an unsaturated monomer other than the nonionic unsaturated monomer having Tg of 60° C. or higher and the cationic unsaturated monomer are not particularly limited, and may be a repeating unit derived from an unsaturated monomer capable of being copolymerized with the nonionic unsaturated monomer having Tg of 60° C. or higher and the cationic unsaturated monomer. Examples of the repeating unit derived from an unsaturated monomer other than the nonionic unsaturated monomer having Tg of 60° C. or higher and the cationic unsaturated monomer include olefins, halogenated olefins, vinyl esters, (meth)acrylates having Tg of lower than 60° C., and (meth)acrylamides having Tg of lower than 60° C.

The sum of contents of the repeating unit derived from the nonionic unsaturated monomer having Tg of 60° C. or higher and the repeating unit derived from the cationic unsaturated monomer in the unsaturated monomer-derived polymer segment as a side chain of the organopolysiloxane graft polymer of the present invention is preferably not less than 70% by mass, more preferably not less than 80% by mass, still more preferably not less than 90% by mass, even still more preferably not less than 95% by mass, and further even still more preferably 100% by mass, from the viewpoints of a good hair settability, a good touch feeling of hair after hair setting and a good hair set retentivity under high humidity conditions upon setting the hair using the hair cosmetic of the present invention, and facilitated removal of the organopolysiloxane graft polymer of the present invention upon shampooing.

<Construction of Organopolysiloxane Graft Polymer>

The content of the organopolysiloxane segment in the organopolysiloxane graft polymer of the present invention is not less than 35% by mass, preferably not less than 40% by mass, and more preferably not less than 45% by mass, from the viewpoints of a good hair settability, a good touch feeling of hair after hair setting and a good hair set retentivity under high humidity conditions upon setting the hair using the hair cosmetic of the present invention, and is also not more than 70% by mass, preferably not more than 65% by mass, and more preferably not more than 60% by mass, from the viewpoints of a good hair settability and a good hair set retentivity under high humidity conditions upon setting the hair using the hair cosmetic of the present invention.

The number-average molecular weight (MNg) of the organopolysiloxane segment being present between the adjacent unsaturated monomer-derived polymer segments (hereinafter also referred to merely as a "molecular weight between graft points") is preferably not less than 500, more preferably not less than 700, still more preferably not less than 1,000, and even still more preferably not less than 1,500, and is also preferably not more than 20,000, more preferably not more than 10,000, still more preferably not more than 4,000, and even still more preferably not more than 3,000, from the viewpoints of a good hair settability and a good hair set retentivity under high humidity conditions upon setting the hair with the hair cosmetic of the present invention.

The "organopolysiloxane segment being present between the adjacent unsaturated monomer-derived polymer segments" as used herein means a portion surrounded by a broken line as shown in the following formula (4) which is located between a bonding point (bonding point A) at which the unsaturated monomer-derived polymer segment is bonded to the organopolysiloxane segment and a bonding point (bonding point B) at which the unsaturated monomer-derived polymer segment adjacent to the above polymer segment is bonded to the organopolysiloxane segment, i.e., means the segment constituted of one $R^1SiO$ unit, one $R^2$ group and $R^1{}_2SiO$ units in the number of y+1.

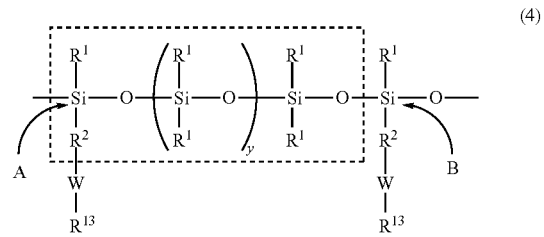

In the above formula (4), $R^1$ groups are each independently an alkyl group having 1 to 22 carbon atoms or an aryl group having 6 to 14 carbon atoms; $R^2$ is an alkylene group that may contain a hetero atom; —W—$R^{13}$ is an unsaturated monomer-derived polymer segment in which $R^{13}$ is a residue of a polymerization initiator; and y is a positive number.

The molecular weight between graft points is an average value of molecular weights of the portions surrounded by a broken line in the above formula, and may be construed as a mass (g/mol) of the organopolysiloxane segment per one mole of the unsaturated monomer-derived polymer segment. In the case where the graft polymer of the present invention is produced from the below-mentioned radical-reactive organopolysiloxane, and all of the radical-reactive functional groups are bonded to the unsaturated monomer-derived polymer segment, the molecular weight between graft points is also regarded as being identical to an inverse number of a molar number (mol/g) of the radical-reactive functional groups that are present per a unit mass of the radical-reactive organopolysiloxane.

In addition, the weight-average molecular weight (MWsi) of the organopolysiloxane segment constituting the main chain of the graft polymer is preferably not less than 5,000, more preferably not less than 10,000, and still more preferably not less than 20,000, from the viewpoints of a good availability of the below-mentioned radical-reactive organopolysiloxane and a good hair settability upon setting the hair using the hair cosmetic of the present invention. Also, MWsi is preferably not more than 200,000, more preferably not more than 150,000, still more preferably not more than 100,000, and even still more preferably not more than 60,000, from the viewpoint of a good water dispersibility of the graft polymer of the present invention.

In the case where the organopolysiloxane graft polymer of the present invention is produced from the below-mentioned radical-reactive organopolysiloxane, the organopolysiloxane segment has a skeleton common to that of the radical-reactive organopolysiloxane, and therefore MWsi is substantially the same as a weight-average molecular weight (MWra) of the radical-reactive organopolysiloxane. For this reason, in the present invention, MWsi is regarded as being the same as MWra. Meanwhile, MWra is a value calculated in terms of a polystyrene from such a molecular weight as measured by a gel filtration chromatography (GPC) under the measuring conditions described in Examples below.

<Process for Producing Organopolysiloxane Graft Polymer>

Next, the process for producing the graft polymer of the present invention is described. The process for producing the graft polymer of the present invention is not particularly limited. For example, there may be used (i) a graft-onto method (polymer reaction method) in which an organopolysiloxane containing a reactive functional group is reacted with an unsaturated monomer-derived polymer segment containing an end functional group capable of reacting the reactive functional group; (ii) a graft-from method in which the unsaturated monomer is subjected to radical polymerization in the presence of a radical-reactive organopolysiloxane; or the like. Of these methods, from the viewpoint of reducing a burden upon production of the graft polymer, preferred is (ii) the graft-from method in which the unsaturated monomer is subjected to radical polymerization in the presence of the radical-reactive organopolysiloxane.

In the following, the process for producing the graft polymer of the present invention by the graft-from method is described.

(Radical-Reactive Organopolysiloxane)

The graft polymer of the present invention can be produced by subjecting unsaturated monomers including the nonionic unsaturated monomer having a glass transition temperature Tg of 60° C. or higher and the cationic unsaturated monomer in the presence of the radical-reactive organopolysiloxane represented by the following general formula (5) or (6).

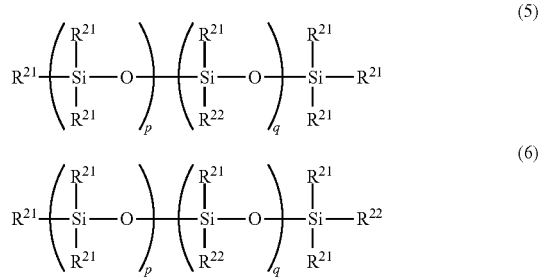

In the above general formulae (5) and (6), $R^{21}$ groups are each independently an alkyl group having 1 to 22 carbon atoms or an aryl group having 6 to 14 carbon atoms; and $R^{22}$ is an alkyl group containing a radical-reactive functional group (hereinafter also referred to as a "radical reactive group-containing alkyl group").

The preferred forms of $R^{21}$ in the above general formulae (5) and (6) are the same as the preferred forms of $R^1$ in the above general formulae (1) and (2).

The suffixes p and q in the above general formulae (5) and (6) have the same meanings as p and q in the above general formulae (1) and (2), and the preferred forms of p and q in the above general formulae (5) and (6) are the same as the preferred forms of p and q in the above general formulae (1) and (2).

The radical-reactive functional group as used in the present invention means a functional group capable of generating a radical. Examples of the radical-reactive functional group include an ethylenically unsaturated group, a halogeno group such as a chloro group and a bromo group, and a sulfanyl group (mercapto group). Of these radical-reactive functional groups, the radical-reactive functional groups containing a sulfanyl group are preferred from the viewpoints of a high reactivity with the unsaturated monomer and a well-controlled molecular weight of the resulting polymer.

In the above general formulae (5) and (6), the number of carbon atoms of the alkyl group in the radical-reactive group-containing alkyl group represented by $R^{22}$ is preferably not less than 2, and more preferably not less than 3, from the viewpoint of a good availability of the radical-reactive organopolysiloxane, and is also preferably not more than 20, more preferably not more than 15, still more preferably not more than 10, and even still more preferably not more than 8, from the viewpoint of a good water dispersibility of the graft polymer of the present invention.

Meanwhile, in the present invention, the number of carbon atoms of the radical-reactive group-containing alkyl group does not include the number of carbon atoms of the radical-reactive functional group even though the radical-reactive functional group contains any carbon atoms, and also does not include the number of carbon atoms of a monovalent substituent group even though the radical-reactive group-containing alkyl group is substituted with the monovalent group.

In the above general formulae (5) and (6), the radical-reactive group-containing alkyl group represented by $R^{22}$ may be substituted with at least one substituent group selected from the group consisting of a hydroxy group, an amino group, a $(C_1-C_3)$alkyl amino group, a di-$(C_1-C_3)$alkyl amino group, an amide group obtained by dehydration condensation of an amino group and a fatty acid having 2 to 4 carbon atoms, a carboxy group, and a $(C_1-C_3)$alkyl ester group. Of these substituent groups, from the viewpoint of a good availability of the raw materials upon production of the radical-reactive organopolysiloxane, preferred is an acetamide group, a $(C_1-C_3)$alkyl amino group or an amino group.

In the above general formulae (5) and (6), the alkyl group in the radical-reactive group-containing alkyl group represented by $R^{22}$ may be interrupted by at least one atom or functional group selected from the group consisting of an oxygen atom, a sulfur atom, —NH—, —COO—, —NHCO— and —NR$^{23}$CO—. In the above —NR$^{23}$CO—, $R^{23}$ is an alkyl group having 1 to 3 carbon atoms. When the radical-reactive group-containing alkyl group is interrupted, from the viewpoints of a good availability and facilitated production of the radical-reactive organopolysiloxane, the radical-reactive group-containing alkyl group is preferably interrupted by —NHCO—.

Specific examples of the radical-reactive group-containing alkyl group used in the present invention includes those groups represented by the following formulae (xvii) to (xx). Of these groups, from the viewpoints of facilitated production and a good availability of the radical-reactive organopolysiloxane, preferred are those groups represented by the following formula (xix) or (xx). $Y^{21}$ and $R^{24}$ in the formula (xx) as well as the preferred forms thereof are the same as $Y^1$ and $R^4$ in the formula (xii) as well as the preferred forms thereof.

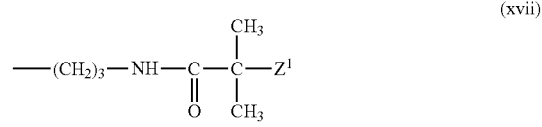

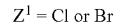

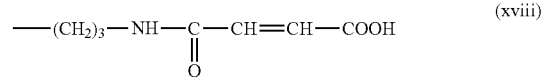

As described above, in the present invention, the weight-average molecular weight (MWra) of the radical-reactive organopolysiloxane is regarded as being the same as the weight-average molecular weight (MWsi), and therefore the preferred forms of MWra are the same as the preferred forms of MWsi.

Meanwhile, MWra is a value calculated in terms of a polystyrene from such a molecular weight as measured by GPC under the measuring conditions described in Examples below.

The number of moles of the radical-reactive functional group being present per a unit mass of the radical-reactive organopolysiloxane is preferably not more than 1/500 mol/g, more preferably not more than 1/700 mol/g, still more preferably not more than 1/1,000 mol/g, and even still more preferably not more than 1/1,500 mol/g, from the viewpoints of attaining a good hair settability upon setting the hair with a hair cosmetic containing the organopolysiloxane graft polymer of the present invention and improving a hair style retentivity after the hair setting, and is also preferably not less than 1/10,000 mol/g, more preferably not less than 1/5,000 mol/g, still more preferably not less than 1/3,000 mol/g, and even still more preferably not less than 1/2,500 mol/g, from the viewpoint of a good water dispersibility of the graft polymer of the present invention.

The radical-reactive organopolysiloxane containing a sulfanyl group as the radical-reactive group may be commercially available, and examples of the commercially available radical-reactive organopolysiloxane include "KF-2001" (available from Shin-Etsu Chemical Co., Ltd.; weight-average molecular weight: 16,000; number of moles of a sulfanyl group per a unit mass: 1/1,900 mol/g), etc.

<Reactive Functional Group-Containing Organopolysiloxane>

The radical-reactive organopolysiloxane may also be produced by reacting a reactive functional group-containing organopolysiloxane represented by the following general formula (7) or (8) with a radical reactivity-imparting agent. The reactive functional group-containing organopolysiloxane represented by the following general formula (7) or (8) is readily commercially available as products having various structures.

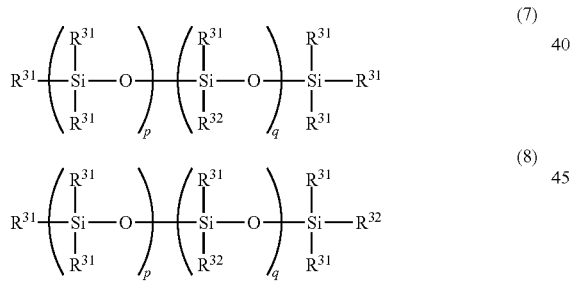

In the above general formulae (7) and (8), $R^{31}$ groups are each independently an alkyl group having 1 to 22 carbon atoms or an aryl group having 6 to 14 carbon atoms; and $R^{32}$ is an alkyl group containing a reactive functional group (hereinafter also referred to as a "reactive group-containing alkyl group"). The suffixes p and q in the above general formulae (7) and (8) have the same meanings as p and q in the above general formulae (5) and (6), and the preferred forms of p and q in the above general formulae (7) and (8) are the same as the preferred forms of p and q in the above general formulae (5) and (6).

The preferred forms of $R^{31}$ in the above general formulae (7) and (8) are the same as the preferred forms of $R^{21}$ in the above general formulae (5) and (6).

The reactive functional group as used in the present invention means a hydroxy group, an amino group, a carboxy group or an epoxy group.

The reactive functional group-containing organopolysiloxane contains at least one substituent group selected from the group consisting of a hydroxy group, an amino group, a carboxy group and an epoxy group.

In the above general formulae (7) and (8), the number of carbon atoms of the reactive group-containing alkyl group represented by $R^{32}$ is preferably not less than 2, and more preferably not less than 3, from the viewpoint of a good availability of the reactive functional group-containing organopolysiloxane, and is also preferably not more than 15, more preferably not more than 10, and still more preferably not more than 5, from the viewpoint of a good water dispersibility of the graft polymer of the present invention.

Specific examples of the reactive group-containing alkyl group used in the present invention include those groups represented by the following formulae (xxi) to (xxviii). Of these reactive group-containing alkyl groups, from the viewpoint of a good availability, preferred is at least one reactive group-containing alkyl group selected from the group consisting of those groups represented by the formulae (xxi) to (xxiv), and from the viewpoint of a high reactivity, more preferred is the reactive group-containing alkyl group represented by the formula (xxiv).

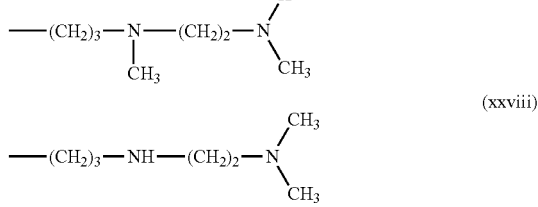

The weight-average molecular weight (MWsim) of the reactive functional group-containing organopolysiloxane is preferably not less than 3,000, more preferably not less than 5,000, still more preferably not less than 10,000, and even still more preferably not less than 20,000, from the viewpoints of attaining a good hair settability upon setting the hair with a hair cosmetic containing the organopolysiloxane graft polymer of the present invention and improving a hair style retentivity after the hair setting, and is also preferably not more than 200,000, more preferably not more than 150,000, still more preferably not more than 100,000, and even still more preferably not more than 60,000, from the viewpoint of a good water dispersibility of the graft polymer of the present invention.

Meanwhile, MWsim used in the present invention is a value calculated in terms of a polystyrene from such a molecular weight as measured by GPC under the measuring conditions described in Examples below.

The number of moles of the reactive functional group being present per a unit mass of the reactive functional group-containing organopolysiloxane is preferably not more than 1/500 mol/g, more preferably not more than 1/700 mol/g, still more preferably not more than 1/1,000 mol/g, and even still more preferably not more than 1/1,500 mol/g, from the viewpoints of attaining a good hair settability upon setting the hair with a hair cosmetic containing the organopolysiloxane graft polymer of the present invention and improving a hair style retentivity after the hair setting, and is also preferably not less than 1/10,000 mol/g, more preferably not less than 1/5,000 mol/g, still more preferably not less than 1/3,000 mol/g, and even still more preferably not less than 1/2,500 mol/g, from the viewpoint of a good water dispersibility of the graft polymer of the present invention.

(Radical Reactivity-Imparting Agent)

The radical reactivity-imparting agent as used in the present invention means a reagent capable of reacting with the reactive functional group of the reactive functional group-containing organopolysiloxane to add a radical-reactive functional group to the reactive functional group-containing organopolysiloxane.

As the radical reactivity-imparting agent, there may be used those compounds containing a radical-reactive functional group and at least one functional group selected from the group consisting of a carboxy group, an ester group, an epoxy group, a hydroxy group and lactones, in a molecule thereof, and unsubstituted or substituted thiolactones.

The radical-reactive functional group of the radical reactivity-imparting agent and the preferred forms thereof are the same as the radical-reactive functional group of the radical-reactive organopolysiloxane and the preferred forms thereof. Of these radical reactivity-imparting agents, from the viewpoint of a high reactivity upon polymerization, preferred are those radical reactivity-imparting agents containing a sulfanyl group (mercapto group), for example, compounds containing a sulfanyl group and a carboxy group in a molecule thereof such as 3-mercapto propionic acid, and lactones containing a sulfanyl group such as γ-butyrolactone thiol. Also, as the unsubstituted or substituted thiolactones, there may be mentioned γ-thiobutyrolactone, N-acetyl-DL-homocysteine thiolactone, DL-homocysteine thiolactone hydrochloride, or the like. Of these radical reactivity-imparting agents, from the viewpoints of a high reactivity with the reactive organopolysiloxane and a high reactivity upon the polymerization, more preferred is N-acetyl-DL-homocysteine thiolactone.

The amount of the radical reactivity-imparting agent used is preferably not less than 0.8 equivalent, more preferably not less than 0.9 equivalent, and still more preferably not less than 0.95 equivalent, on the basis of a total amount of the reactive functional group of the reactive functional group-containing organopolysiloxane, from the viewpoint of a high reactivity. Also, the amount of the radical reactivity-imparting agent used is preferably not more than 1.2 equivalent, more preferably not more than 1.1 equivalent, and still more preferably not more than 1.05 equivalent, on the basis of a total amount of the reactive functional group of the reactive functional group-containing organopolysiloxane, from the viewpoint of reducing an amount of the radical reactivity-imparting agent that remains unreacted after the reaction.

(Production of Radical-Reactive Organopolysiloxane)

The reaction between the radical reactivity-imparting agent and the reactive functional group-containing organopolysiloxane may be carried out in the presence of a solvent.

Examples of the solvent include water; alcohols such as methanol, ethanol and isopropanol; ketones such as acetone and methyl ethyl ketone; esters such as ethyl acetate and butyl acetate; hydrocarbons such as hexane and cyclohexane; ethers such as diethyl ether and tetrahydrofuran; aromatic compounds such as benzene and toluene; and halogenated hydrocarbons such as dichloromethane and chloroform.

From the viewpoint of reducing an environmental burden, it is preferred that no solvent is used in the above reaction.

The reaction temperature is preferably not lower than 50° C., more preferably not lower than 70° C., and still more preferably not lower than 90° C., from the viewpoint of a high reactivity, and is also preferably not higher than 200° C., more preferably not higher than 150° C., and still more preferably not higher than 120° C., from the viewpoint of a good chemical stability of the resulting radical-reactive polysiloxane.

The reaction time is preferably not less than 1 h, and more preferably not less than 2 h, from the viewpoint of allowing the reaction to proceed sufficiently, and is also preferably not more than 10 h, and more preferably not more than 5 h, from the viewpoint of a high productivity.

From the viewpoint of a high reactivity of the resulting radical-reactive organopolysiloxane, the reaction between the functional group of the reactive organopolysiloxane and the radical reactivity-imparting agent is preferably carried out until the reaction proceeds to a rate of not less than 50%, more preferably not less than 80%, still more preferably not less than 90%, and even still more preferably not less than 95%.

The method of measuring the respective conversion rates may vary depending upon the reactive functional group of the reactive functional group-containing organopolysiloxane and the radical reactivity-imparting agent used in the reaction, and any of the conversion rates may be measured by known methods. For example, in the case where the reactive functional group of the reactive functional group-containing organopolysiloxane is an amino group, and the radical reactivity-imparting agent is a thiolactone, the conversion rate of the amino group may be determined by "Testing Method for Total Base Number of Petroleum Products (perchloric acid method)" (JIS K 2501), and the conversion rate of the thiolactones may be determined by a gas chromatographic method.

(Polymerization of Unsaturated Monomer)

The method of subjecting the unsaturated monomers to polymerization in the presence of the radical-reactive organopolysiloxane is not particularly limited, and there may be adopted a bulk polymerization method, a solution polymerization method and a suspension polymerization method, etc. Of these polymerization methods, preferred is a solution polymerization method.

The amount of the unsaturated monomers used as the raw material is preferably not less than 30% by mass, more preferably not less than 35% by mass, and still more preferably not less than 40% by mass, on the basis of a total amount of the radical-reactive organopolysiloxane and the unsaturated monomers, from the viewpoint of a good water dispersibility of the graft polymer of the present invention. Also, from the viewpoints of a good hair settability and a good hair set retentivity under high humidity conditions upon setting the hair using the hair cosmetic of the present invention, the amount of the unsaturated monomers used is preferably not more than 65% by mass, more preferably not more than 60% by mass, and still more preferably not more than 55% by mass, on the basis of a total amount of the radical-reactive organopolysiloxane and the unsaturated monomers.

The content of the nonionic unsaturated monomer having Tg of 60° C. or higher (except for an unsaturated monomer containing an amino group) in the unsaturated monomers used as the raw materials is preferably not less than 40% by mass, more preferably not less than 45% by mass, and still more preferably not less than 50% by mass, on the basis of a total amount of the whole unsaturated monomers, from the viewpoint of a good hair set retentivity under high humidity conditions after setting the hair using the hair cosmetic of the present invention. Also, the content of the nonionic unsaturated monomer having Tg of 60° C. or higher (except for an unsaturated monomer containing an amino group) in the unsaturated monomers used as the raw materials is preferably not more than 90% by mass, more preferably not more than 85% by mass, and still more preferably not more than 80% by mass, on the basis of a total amount of the whole unsaturated monomers, from the viewpoint of a good touch feeling of hair after setting the hair with the hair cosmetic of the present invention.

Specific examples of the nonionic unsaturated monomer having Tg of 60° C. or higher (except for an unsaturated monomer containing an amino group) in the unsaturated monomers used as the raw materials, and the preferred forms thereof are the same as the specific examples as described in the above item concerning the "repeating unit derived from nonionic unsaturated monomer having Tg of 60° C. or higher", and the preferred forms thereof.

The content of the cationic unsaturated monomer in the unsaturated monomers used as the raw materials is preferably not less than 10% by mass, more preferably not less than 15% by mass, and still more preferably not less than 20% by mass, on the basis of a total amount of the whole unsaturated monomers, from the viewpoints of a good hair settability after setting hair using the hair cosmetic of the present invention and a good washability. Also, the content of the cationic unsaturated monomer in the unsaturated monomers used as the raw materials is preferably not more than 60% by mass, more preferably not more than 55% by mass, and still more preferably not more than 50% by mass, on the basis of a total amount of the whole unsaturated monomers, from the viewpoint of a good hair settability after setting hair using the hair cosmetic of the present invention.

The cationic unsaturated monomer in the unsaturated monomers used as the raw materials, and the preferred forms thereof are the same as the cationic unsaturated monomer as described in the above item concerning the "repeating unit derived from cationic unsaturated monomer", and the preferred forms thereof.

Furthermore, the unsaturated monomers used as the raw materials may also contain an unsaturated monomer other than the nonionic unsaturated monomer having Tg of 60° C. or higher and the cationic unsaturated monomer.

The other unsaturated monomer may be any unsaturated monomer as long as it can be copolymerized with the nonionic unsaturated monomer, having Tg of 60° C. or higher and the cationic unsaturated monomer.

Specific examples of the other unsaturated monomer include olefins, halogenated olefins, vinyl esters, (meth)acrylates having Tg of lower than 60° C., and (meth)acrylamides having Tg of lower than 60° C.

The sum of contents of the nonionic unsaturated monomer having Tg of 60° C. or higher and the cationic unsaturated monomer in the unsaturated monomers as the raw materials is preferably not less than 70% by mass, more preferably not less than 80% by mass, still more preferably not less than 90% by mass, and even still more preferably not less than 95% by mass, and is also preferably not more than 100% by mass, from the viewpoints of a good hair settability, a good touch feeling of hair after the hair setting and a good hair set retentivity under high humidity conditions upon setting the hair using the hair cosmetic of the present invention, and facilitated removal of the organopolysiloxane graft polymer of the present invention upon shampooing.

In the case where the unsaturated monomers are polymerized by a solution polymerization method, the solvent used therein is not particularly limited as long as any of the radical-reactive organopolysiloxane and the unsaturated monomers as the raw materials as well as the obtained graft polymer of the present invention can be dissolved or uniformly dispersed therein.

Specific examples of the solvent include water; alcohols such as methanol, ethanol and isopropanol; ketones such as acetone and methyl ethyl ketone; esters such as ethyl acetate and butyl acetate; hydrocarbons such as hexane and cyclohexane; ethers such as diethyl ether and tetrahydrofuran; aromatic compounds such as benzene and toluene; and halogenated hydrocarbons such as dichloromethane and chloroform. These solvents may be used alone or in combination of any two or more thereof.

Of these solvents, from the viewpoint of obtaining the graft polymer of the present invention which has a more uniform side chain molecular weight distribution, it is preferred to use at least one solvent selected from the group consisting of water; alcohols having not less than 1 and not more than 8 carbon atoms such as ethanol and isopropanol; esters having not less than 2 and not more than 8 carbon atoms such as ethyl acetate and butyl acetate; and ethers having not less than 2 and not more than 8 carbon atoms such as diethyl ether and tetrahydrofuran. Further, from the viewpoint of bringing the solvent into products upon production thereof when using the graft polymer of the present invention in the applications of a hair cosmetic, etc., it is more preferred to use at least one solvent selected from the group consisting of water, and alcohols having not less than 1 and not more than 3 carbon atoms such as ethanol.

The amount of the solvent used is not particularly limited as long as any of the radical-reactive organopolysiloxane and the unsaturated monomers as the raw materials as well as the obtained organopolysiloxane graft polymer of the present invention can be dissolved or uniformly dispersed therein. From the viewpoints of a facilitated operation upon production of the graft polymer, the amount of the solvent used is preferably not less than 60% by mass, more preferably not less than 80% by mass, and still more preferably not less than 100% by mass, on the basis of a total amount of the radical-reactive organopolysiloxane and the unsaturated monomers charged upon the production of the graft polymer. Also, from the viewpoint of a high reactivity, the amount of the solvent used is preferably not more than 900% by mass, more preferably not more than 400% by mass, still more preferably not more than 200% by mass, and even still more preferably not more than 150% by mass, on the basis of a total amount of the radical-reactive organopolysiloxane and the unsaturated monomers charged upon the production of the graft polymer.

Examples of the polymerization initiator include azo-based initiators such as 2,2'-azobisisobutyronitrile and 2,2'-azobis(2,4-dimethyl valeronitrile); peroxide-based initiators such as lauroyl peroxide and benzoyl peroxide; and persulfate-based initiators such as ammonium persulfate. Also, the polymerization may be initiated by generating a radical by irradiation of light, etc. The amount of the polymerization initiator used is not particularly limited. The amount of the polymerization initiator used is preferably not more than 10% by mass, more preferably not more than 5% by mass, and still more preferably not more than 2% by mass, on the basis of a total amount of the unsaturated monomers charged, from the viewpoint of a well-controlled weight-average molecular weight of the resulting graft polymer of the present invention, and is also preferably not less than 0.01% by mass, more preferably not less than 0.1% by mass, and still more preferably not less than 0.5% by mass, on the basis of a total amount of the unsaturated monomers charged, from the viewpoint of a high reactivity.

The temperature used upon the polymerization reaction may be appropriately selected according to the kinds of polymerization initiator and solvent used, etc., and is usually preferably not lower than 50° C., and more preferably not lower than 60° C., from the viewpoint of a high polymerization reaction rate. The polymerization reaction is preferably carried out under normal pressures in order to reduce a burden on facilities used for the polymerization reaction. From the viewpoint of carrying out the reaction at a temperature not higher than a boiling point of the solvent, the temperature used upon the polymerization reaction is preferably not higher than 120° C., more preferably not higher than 100° C., still more preferably not higher than 90° C., and even still more preferably not higher than 80° C.

The polymerization reaction is preferably carried out until the conversion rate of the unsaturated monomers reaches not less than 80%, and more preferably not less than 90%. The conversion rate of the unsaturated monomers may be measured by the method described in Examples below.

The polymerization reaction time is usually not less than 0.1 h and not more than 60 h, and is preferably not less than 0.5 h, and more preferably not less than 1 h, from the viewpoint of facilitated operation of the reaction, and is also preferably not more than 30 h, more preferably not more than 20 h, and still more preferably not more than 10 h, from the viewpoint of a high productivity. During the polymerization reaction, in the case where the raw materials are added dropwise, the polymerization reaction time includes the time required for dropwise addition of the raw materials. The polymerization reaction time can be controlled by suitably varying the polymerization reaction temperature.

The radical-reactive organopolysiloxane and the unsaturated monomers as the raw materials, the solvent, the polymerization initiator, etc., may be added at one time to conduct the polymerization reaction. Alternatively, in order to control the composition of the resulting product, the polymerization reaction may be carried out by adding these components in a split addition manner or in a dropwise addition manner, etc., i.e., in an intermittent or continuous manner over a predetermined period of time. For example, there may be used (1) a method in which the radical-reactive organopolysiloxane, the unsaturated monomers and the solvent are mixed and heated, and then a solution into which the polymerization initiator is dissolved is added at one time or dropwise to the resulting mixture; (2) a method in which the solvent is heated, and then the radical-reactive organopolysiloxane, the unsaturated monomers and the polymerization initiator are each independently added to the solvent, or a solution prepared by mixing and dissolving these components in the solvent is added dropwise thereto; (3) a method in which the radical-reactive organopolysiloxane, a part of the unsaturated monomers and the solvent are mixed and heated, and then a solution in which the polymerization initiator and a remaining part of the unsaturated monomers are dissolved is added at one time or dropwise to the resulting mixture; or the like.

In addition, after completion of the polymerization reaction, the resulting product may be subjected to purification treatments, reduction in amounts of the unreacted unsaturated monomers remaining in the product or the like by known methods, if required. For example, the amounts of the unreacted unsaturated monomers and other impurities in the product may be reduced by heating after addition of the polymerization initiator thereto, membrane purification, steam distillation, adsorbent treatment, etc.

The organopolysiloxane graft polymer of the present invention may be produced by the aforementioned method. Alternatively, the organopolysiloxane graft polymer of the present invention may also be produced by the process for producing an organopolysiloxane graft polymer according to the present invention.

That is, the organopolysiloxane graft polymer of the present invention may be produced by the process for producing an organopolysiloxane graft polymer including an organopolysiloxane segment as a main chain thereof and an unsaturated monomer-derived polymer segment as a side chain thereof, said process including the step of polymerizing unsaturated monomers including a nonionic unsaturated monomer having a glass transition temperature Tg of 60° C. or higher and a cationic unsaturated monomer in the presence of a radical-reactive organopolysiloxane represented by the following general formula (5) or (6), in which a content of the organopolysiloxane segment in the organopolysiloxane graft polymer is not less than 35% by mass and not more than 70% by mass, and the unsaturated monomer-derived polymer segment contains a repeating unit derived from the nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from the cationic unsaturated monomer in an amount of not less than 10% by mass and not more than 60% by mass.

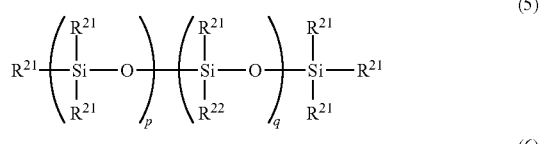

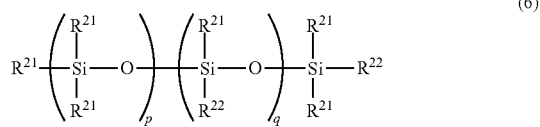

In the general formulae (5) and (6), $R^{21}$ groups are each independently an alkyl group having not less than 1 and not more than 22 carbon atoms or an aryl group having not less than 6 and not more than 14 carbon atoms; $R^{22}$ is an alkyl group containing a radical-reactive functional group; p is a number of not less than 2 and not more than 4,000; and q is a number of not less than 2 and not more than 500, in which repeating units in the number of p and repeating units in the number of q may be bonded to each other either in a block form or in a random form.

In the process for producing the organopolysiloxane graft polymer according to the present invention, the compounds, amounts, ratios and conditions used therein are the same as the aforementioned respective preferred ranges. For example, the aforementioned radical-reactive organopolysiloxane is preferably produced by reacting a reactive functional group-containing organopolysiloxane represented by the following general formula (7) or (8) with a radical reactivity-imparting agent.

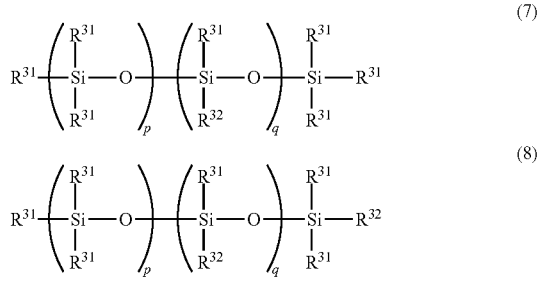

(7)

(8)

In the above general formulae (7) and (8), $R^{31}$ groups are each independently an alkyl group having 1 to 22 carbon atoms or an aryl group having 6 to 14 carbon atoms; $R^{32}$ is an alkyl group containing a reactive functional group; p is a number of not less than 2 and not more than 4,000; and q is a number of not less than 2 and not more than 500, in which repeating units in the number of p and repeating units in the number of q may be bonded to each other either in a block form or in a random form.

[Hair Cosmetic]

(Graft Polymer of the Present Invention (Component (A)))

The hair cosmetic of the present invention contains the graft polymer of the present invention (hereinafter also referred to as a "component (A)"). By incorporating the graft polymer of the present invention into the hair cosmetic, it is possible to attain a soft touch, a hair settability that is free from change of a hair style even upon combing of hand or fingers through hair, and a more natural finish feeling.

The content of the component (A) in the hair cosmetic is preferably not less than 0.01% by mass, more preferably not less than 0.05% by mass, still more preferably not less than 0.1% by mass, and even still more preferably not less than 0.5% by mass, and is also preferably not more than 50% by mass, more preferably not more than 30% by mass, still more preferably not more than 20% by mass, and even still more preferably not more than 10% by mass, on the basis of a total mass of the hair cosmetic (however, in the case of a spray-type hair cosmetic containing a propellant, a mass of the propellant is excluded from the total mass of the hair cosmetic), from the viewpoints of a good hair settability of the hair cosmetic of the present invention, a good hair set persistence and a good washability. By controlling the content of the component (A) in the hair cosmetic to the above-specified range, in particular, when using the below-mentioned organic solvent in combination with an organic acid or a salt thereof, it is possible to further enhance both a hair settability and a hair style retentivity after hair setting without inhibiting a hair modifying effect by the organic acid and organic solvent (such as enhancement in hair manageability).

(Solvent)

The hair cosmetic of the present invention may also contain, in addition to the above components, at least one solvent selected from the group consisting of water and straight-chain or branched-chain, saturated or unsaturated alcohols having not less than 1 and not more than 3 carbon atoms, from the viewpoints of a hair settability, a good feeling of use and facilitated operation upon preparation of the hair cosmetic. Of these solvents, preferred is at least one solvent selected from the group consisting of water, ethanol and isopropanol, and more preferred is at least one solvent selected from the group consisting of water and ethanol.

(Organic Solvent (Component (B)))

In addition, the hair cosmetic of the present invention may further contain an organic solvent selected from the group consisting of the following compounds (b1) to (b5) (hereinafter referred to as a "component (B)") as a preferred component from the viewpoints of attaining an effect of improving bounce and body of hair, an effect of improving softness and manageability of hair, promotion of modifying effects of hair (such as resilience improving effect and moisture resistance improving effect, etc.), and enhancing a hair settability by compatibilizing the component (B) with the component (A).

(b1) Compounds represented by the general formula (9):

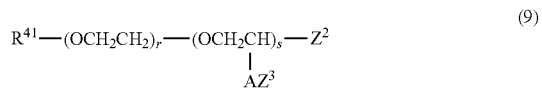

(9)

wherein $R^{41}$ is a hydrogen atom, an alkyl group having 1 to 6 carbon atoms or a group represented by $R^{42}$-Ph-$R^{43}$— wherein $R^{42}$ is a hydrogen atom, a methyl group or a methoxy group, $R^{43}$ is a bond or a divalent saturated or unsaturated hydrocarbon group having 1 to 3 carbon atoms, and Ph is a p-phenylene group; A is a bond or a divalent saturated hydrocarbon group having 1 to 4 carbon atoms; $Z^2$ and $Z^3$ are each independently a hydrogen atom or a hydroxy group; and r and s are each independently a number of 0 to 5 with the proviso that when r and s are 0 (r=s=0), $Z^2$ is a hydroxy group, and $R^{41}$ is not any of a hydrogen atom, an alkyl group having 1 to 3 carbon atoms and a group represented by $R^{42}$-Ph-.

(b2) N-alkyl pyrrolidones or N-alkenyl pyrrolidones containing an alkyl group having 1 to 18 carbon atoms or an alkenyl group, which is bonded to a nitrogen atom therein.

(b3) Alkylene carbonates having 2 to 4 carbon atoms.

(b4) Polypropylene glycols having a number-average molecular weight of from 200 to 1,000.

(b5) Lactones or cyclic ketones represented by the general formula (10), (11) or (12):

(10)

(11)

(12)

wherein $Y^{41}$ to $Y^{43}$ are respectively a methylene group or an oxygen atom; $R^{44}$ and $R^{45}$ are substituent groups that are different from each other; and a and b are each independently 0 or 1.

Examples of the compound (b1) among the organic solvents as the component (B) include $C_4$ to $C_6$ straight-chain or branched-chain aliphatic alcohols such as butanol and isobutanol, ethylene glycol, propylene glycol, dipropylene glycol, 1,3-butanediol, benzyl alcohol, cinnamyl alcohol, phenethyl alcohol, p-anisyl alcohol, p-methyl benzyl alcohol, phenoxyethanol, 2-benzyloxy ethanol, methyl carbitol, ethyl carbitol, propyl carbitol, butyl carbitol, triethylene glycol monoethyl ether and triethylene glycol monobutyl ether.

Examples of the compound (b2) include N-methyl pyrrolidone, N-octyl pyrrolidone and N-lauryl pyrrolidone.

Examples of the compound (b3) include ethylene carbonate and propylene carbonate.

The polypropylene glycols having a number-average molecular weight of from 200 to 1,000 as the compound (b4) preferably have a number-average molecular weight of from 300 to 500. Meanwhile, the number-average molecular weight means a number-average molecular weight as measured by GPC in terms of polystyrene.

In the compound (b5), $R^{44}$ and $R^{45}$ in the general formulae (10) to (12) are respectively preferably a straight-chain, branched-chain or cyclic alkyl group, a hydroxy group, a sulfonic acid group, a phosphoric acid group, a carboxy group, a phenyl group, a sulfoalkyl group, an alkyl phosphate group or a carboxyalkyl group. Among these groups, straight-chain or branched-chain alkyl groups having 1 to 6 carbon atoms, for example, a methyl group, an ethyl group, a propyl group, an isopropyl group, a butyl group, etc., are more preferred. These groups are preferably bonded to a γ-position in the case where the compound (b5) is γ-lactone or a δ-position in the case where the compound (b5) is δ-lactone (i.e., methylene adjacent to a hetero oxygen atom). When it is intended to increase a water solubility of the respective compounds represented by the general formulae (10) to (12), $R^{44}$ or $R^{45}$ preferably contains an acid group such as a sulfonic acid group, a phosphoric acid group and a carboxy group, or an alkyl group substituted with the acid group.

Examples of the lactones among these compounds (b5) include γ-butyrolactone, γ-caprolactone, γ-valerolactone, δ-valerolactone, δ-caprolactone and δ-heptanolactone. From the viewpoint of a good stability of these lactones, preferred are γ-lactones, in particular, γ-butyrolactone and γ-caprolactone.

Examples of the cyclic ketones among the compounds (b5) include cyclopentanone, cyclohexanone, cycloheptanone and 4-methyl cycloheptanone.

In addition, the component (B) used in the present invention is preferably kept in a liquid state at 25° C. from the viewpoint of promotion of penetration of the component (B).

Further, from the viewpoint of promotion of penetration of the component (B), C log P of the component (B) is preferably from −2 to 3, and more preferably from −1 to 2. The parameter C log P as used herein means a calculation value of an octanol/water partition coefficient (log P) defined by the following formula (I) as a scale representing partition of substances between an octanol phase and a water phase, examples of which are described in "Chemical Reviews", Vol. 71, No. 6 (1971).

$$\log P = \log([\text{substance}]_{Octanol}/[\text{substance}]_{Water}) \qquad (I)$$

wherein [substance]$_{Octanol}$ is a molar concentration of the substance in a 1-octanol phase; and [substance]$_{Water}$ is a molar concentration of the substance in a water phase.

Concrete values of C log P of main compounds as the component (B) are as follows: dipropylene glycol (−0.67), 1,3-butanediol (−0.29), benzyl alcohol (1.1), 2-benzyloxy ethanol (1.2), 2-phenyl ethanol (1.2), 1-phenoxy-2-propanol (1.1), polypropylene glycol 400 (0.9), propylene carbonate (−0.41), and γ-butyrolactone (−0.64). Of these components (B), preferred are benzyl alcohol and 2-benzyloxy ethanol.

These components (B) may be used in combination of any two or more thereof. The total content of the compounds as the component (B) in the hair cosmetic is preferably from 0.1 to 40% by mass, more preferably from 0.5 to 10% by mass, and still more preferably from 1 to 5% by mass, from the viewpoints of a good effect of improving bounce and body of hair, a good effect of improving softness and manageability of hair, promotion of modifying effect of hair (such as resilience improving effect and moisture resistance improving effect), and a good effect of enhancing a hair settability by using the component (B) in combination with the component (A).

(Organic Carboxylic Acid or Salt Thereof (Component (C)))

Also, the hair cosmetic used in the present invention may contain, together with the component (B), an organic carboxylic acid or a salt thereof which may contain a hydroxy group (hereinafter referred to as a "component (C)") from the viewpoints of attaining an inside modifying effect of hair (such as hollowness mending effect), an effect of improving bounce and body of hair, an effect of improving softness and manageability of hair, and enhancing a hair settability by compatibilizing the component (C) with the component (A).

In this case, from the viewpoint of promotion of penetration of the component (C), preferred examples of the component (B) include dipropylene glycol, 1,3-butanediol, benzyl alcohol, phenoxyethanol, 2-benzyloxy ethanol, propylene carbonate and polypropylene glycol (having a number-average molecular weight of preferably from 300 to 500, more preferably 400).

The organic carboxylic acid as the component (C) is preferably an organic carboxylic acid having 2 to 8 carbon atoms, from the viewpoint of promotion of penetration of the component (C).

Specific examples of the organic carboxylic acid as the component (C) include monocarboxylic acids such as acetic acid and propionic acid; dicarboxylic acids such as malonic acid, succinic acid, glutaric acid, adipic acid, maleic acid, fumaric acid and phthalic acid; polycarboxylic acids such as polyglutamic acid; hydroxycarboxylic acids such as glycolic acid, lactic acid, hydroxyacrylic acid, glyceric acid, malic acid, tartaric acid and citric acid; and acidic amino acids such as glutamic acid and aspartic acid. Of these organic carboxylic acids, from the viewpoint of promotion of penetration of the component (C), preferred are hydroxycarboxylic acids having 2 to 6 carbon atoms, and more preferred are lactic acid and malic acid.

Examples of salts of these organic carboxylic acids include salts of these organic carboxylic acids with an alkali metal, an alkali earth metal, ammonia or an organic amine compound.

These compounds as the component (C) may be used in combination of any two or more thereof. The total content of the compounds as the component (C) in the hair cosmetic is preferably from 0.1 to 30% by mass, more preferably from 0.5 to 20% by mass, and still more preferably from 0.5 to 10% by mass, from the viewpoints of attaining an inside modifying effect of hair (such as hollowness mending effect), an effect of improving bounce and body of hair, an effect of improving softness and manageability of hair, and enhancing a hair settability by using the component (C) in combination with the component (A).

The mass ratio of the organic carboxylic acid or salt thereof as the component (C) to the organic solvent as the component (B) ((C):(B)) is preferably in the range of from 10:1 to 1:7, and more preferably from 4:1 to 1:3, in order to effectively exhibit an inside modifying effect of hair (such as hollowness mending effect), an effect of improving bounce and body of hair, and an effect of improving softness and manageability of hair.

(Set Polymer (Component (D)))

Further, the hair cosmetic used in the present invention may contain, in addition to the component (A) as the set polymer, an additional set polymer (hereinafter referred to as a "component (D)"), if required.

Examples of the additional set polymer as the component (D) include the following polymers 1) to 8). These polymers may be used alone or in combination of any two or more thereof.

1) Vinyl Pyrrolidone-Based Polymer
Polyvinyl Pyrrolidone:

Examples of commercially available products of the polyvinyl pyrrolidone include "LUVISKOL K12" and "LUVISKOL K30" (both available from BASF), "PVP K15" and "PVP K30" (both available from Ashland Inc.), and the like.

Vinyl Pyrrolidone/Vinyl Acetate Copolymer:

Examples of commercially available products of the vinyl pyrrolidone/vinyl acetate copolymer include "LUVISKOL VA28" and "LUVISKOL VA73" (both available from BASF), "PVP/VA E-735" and "PVP/VA S-630" (both available from Ashland Inc.), and the like.

Vinyl Pyrrolidone/Vinyl Acetate/Vinyl Propionate Terpolymer:

Examples of commercially available products of the vinyl pyrrolidone/vinyl acetate/vinyl propionate terpolymer include "LUVISKOL VAP343" (available from BASF), and the like.

Vinyl Pyrrolidone/Alkylaminoacrylate Copolymer:

Examples of commercially available products of the vinyl pyrrolidone/alkylaminoacrylate copolymer include "LUVIFLEX" (available from BASF), "COPOLYMER 845", "COPOLYMER 937" and "COPOLYMER 958" (all available from GAF), and the like.

Vinyl Pyrrolidone/Acrylate/(Meth)Acrylic Acid Copolymer:

Examples of commercially available products of the vinyl pyrrolidone/acrylate/(meth)acrylic acid copolymer include "LUVIFLEX VBM35" (available from BASF), and the like.

Vinyl Pyrrolidone/Alkylaminoacrylate/Vinyl Caprolactam Copolymer:

Examples of commercially available products of the vinyl pyrrolidone/alkylaminoacrylate/vinyl caprolactam copolymer include "COPOLYMER VC-713" (available from Ashland Inc.), and the like.

2) Acidic Vinyl Ether-Based Polymer
Methyl Vinyl Ether/Maleic Anhydride Alkyl Half Ester Copolymer:

Examples of commercially available products of the methyl vinyl ether/maleic anhydride alkyl half ester copolymer include "GANTREZ ES-225", "GANTREZ ES-425" and "GANTREZ SP-215" (all available from Ashland Inc.), and the like.

3) Acidic Polyvinyl Acetate-Based Polymer
Vinyl Acetate/Crotonic Acid Copolymer:

Examples of commercially available products of the vinyl acetate/crotonic acid copolymer include "RESIN 28-1310" (available from AKZO NOBEL), "LUVISET CA66" (available from BASF), and the like.

Vinyl Acetate/Crotonic Acid/Vinyl Neodecanoate Copolymer:

Examples of commercially available products of the vinyl acetate/crotonic acid/vinyl neodecanoate copolymer include "RESIN 28-2930" (available from AKZO NOBEL), and the like.

Vinyl Acetate/Crotonic Acid/Vinyl Propionate Copolymer:

Examples of commercially available products of the vinyl acetate/crotonic acid/vinyl propionate copolymer include "LUVISET CAP" (available from BASF), and the like.

4) Acidic Acrylic Polymer
(Meth)Acrylic Acid/(Meth)Acrylic Acid Ester Copolymer:

Examples of commercially available products of the (meth)acrylic acid/(meth)acrylic acid ester copolymer include "PLUS SIZE L53P" (available from GOO Chemical Co., Ltd.), "DIAHOLD" (available from Mitsubishi Chemical Holdings Corporation), and the like.

Acrylic Acid/Acrylic Acid Alkyl Ester/Alkyl Acrylamide Copolymer:

Examples of commercially available products of the acrylic acid/acrylic acid alkyl ester/alkyl acrylamide copolymer include "ULTRAHOLD 8" (available from BASF), "UNFOAMER V-42" (available from AKZO NOBEL), and the like.

5) Amphoteric Acrylic Polymer
(Meth)Acryl Ethyl Betaine/(Meth)Acrylic Acid Alkyl Ester Copolymer:

Examples of the (meth)acryl ethyl betaine/(meth)acrylic acid alkyl ester copolymer include a copolymer of N-methacryloyloxyethyl-N,N-dimethyl ammonium-α-N-methyl carboxybetaine and a (meth)acrylic acid alkyl ester, and the like, and examples of commercially available products of the (meth)acryl ethyl betaine/(meth)acrylic acid alkyl ester copolymer include "YUKAFOAMER M-75" and "YUKAFOAMER SM" (both available from Mitsubishi Chemical Holdings Corporation), and the like.

Acrylic Acid Alkyl Ester/Butylaminoethyl Methacrylate/Acrylic Acid Octyl Amide Copolymer:

Examples of the acrylic acid alkyl ester/butylaminoethyl methacrylate/acrylic acid octyl amide copolymer include an octyl acrylamide/acrylate/butylaminoethyl methacrylate copolymer and the like, and examples of commercially available products of the acrylic acid alkyl ester/butylaminoethyl methacrylate/acrylic acid octyl amide copolymer include "UNFOAMER 28-4910" (available from AKZO NOBEL), and the like.

6) Basic Acrylic Polymer
Acrylamide/Acrylic Ester-Based Copolymer:

Examples of the acrylamide/acrylic ester-based copolymer include those copolymers described in Examples of JP 2-180911A and JP 8-291206A, and the like.

7) Cellulose Derivative
Cationic Cellulose Derivative:

Examples of commercially available products of the cationic cellulose derivative include "CELLCOAT H-100" and "CELLCOAT L-200" (both available from AKZO NOBEL), and the like.

8) Chitin/Chitosan Derivative
Hydroxypropyl Chitosan:

Examples of commercially available products of the hydroxypropyl chitosan include "CHITOFILMER" (available from Ichimaru Falcos Co., Ltd.), and the like.

Salt of Carboxymethyl Chitin, Carboxymethyl Chitosan or Chitosan with a Monovalent Acid Such as Pyrrolidone Carboxylic Acid, Lactic Acid and Glycolic Acid or a Divalent Acid Such as Adipic Acid and Succinic Acid:

Examples of commercially available products of the salt include "CHITOMER PC" (pyrrolidone carboxylic acid salt) and "CHITOMER L" (lactic acid salt) (both available from The Dow Chemical Company), and the like.

Of these set polymers, preferred are set polymers selected from acrylic polymers and vinyl pyrrolidone-based polymers. The content of the set polymer in the hair cosmetic is preferably from 0.05 to 20% by mass, more preferably from 0.1 to 10% by mass, and still more preferably from 0.3 to 5% by mass, on the basis of a total mass of the hair cosmetic.

(Conditioning Component)

The hair cosmetic used in the present invention may also contain a conditioning component selected from oil agents and silicones (except for the component (A) of the present invention) for the purpose of further enhancing a conditioning effect of hair.

The oil agents are used for enhancing a feeling of manageability of hair after drying. Examples of the oil agents include hydrocarbons such as squalene, squalane, liquid isoparaffin, light liquid isoparaffin, heavy liquid isoparaffin, α-olefin oligomers, liquid paraffin and cycloparaffin; glycerides such as castor oil, cacao seed oil, mink oil, avocado oil and olive oil; waxes such as beeswaxes, spermaceti, lanolin, microcrystalline waxes, ceresin waxes and carnauba waxes; higher alcohols such as cetyl alcohol, oleyl alcohol, stearyl alcohol, isostearyl alcohol and 2-octyl dodecanol; esters such as octyl dodecyl myristate, hexyl laurate, cetyl lactate, propylene glycol monostearate, oleyl oleate, hexadecyl 2-ethyl hexanoate, isononyl isononanoate and tridecyl isononanoate; higher fatty acids such as capric acid, lauric acid, myristic acid, palmitic acid, stearic acid, behenic acid, oleic acid, coconut oil fatty acid, isostearic acid and isopalmitic acid; solid fats such as cholesterol, vaseline, cholesteryl isostearate and sphingolipid as well as jojoba oil, isostearyl glyceryl ether and polyoxypropylene butyl ether. Of these oil agents, preferred are branched hydrocarbons such as squalene, squalane, liquid isoparaffin, light liquid isoparaffin, heavy liquid isoparaffin and α-olefin oligomers.

The content of the oil agents in the hair cosmetic is preferably from 0.05 to 20% by mass, more preferably from 0.1 to 10% by mass, and still more preferably from 0.5 to 5% by mass, from the viewpoints of a good hair manageability and a less sticky feeling.

Examples of the silicones (except for the component (A) of the present invention) include dimethyl polysiloxane, polyether-modified silicones, amino-modified silicones, carboxy-modified silicones, methyl phenyl polysiloxane, fatty acid-modified silicones, polyglycerin-modified silicones, aliphatic alcohol-modified silicones, epoxy-modified silicones, fluorine-modified silicones, cyclic silicones and alkyl-modified silicones. Of these silicones, preferred are dimethyl polysiloxane, polyether-modified silicones and amino-modified silicones.

The dimethyl polysiloxane is capable of imparting a good lubricating property to hair; the polyether-modified silicones are capable of imparting smoothness to hair; and the amino-modified silicones are capable of imparting a good moist feeling to hair. In the present invention, various silicones may be used alone or in combination of any two or more thereof according to their performances as demanded.

The dimethyl polysiloxane used may have a viscosity ranging from about 5 mm²/s to about 10,000,000 mm²/s at which the dimethyl polysiloxane may be frequently supplied in the from of an emulsion, according to a touch feeling of hair as demanded. The viscosity of the dimethyl polysiloxane is preferably from 5,000 to Ser. No. 10/000,000 mm²/s, and more preferably from 50,000 to Ser. No. 10/000,000 mm²/s. Meanwhile, the above viscosity is a viscosity as measured at 25° C.

The polyether-modified silicones are not particularly limited as long as they may be silicones having a polyoxyalkylene group. Examples of the group constituting the polyoxyalkylene group include an oxyethylene group and an oxypropylene group. Specific examples of the polyether-modified silicones include "KF-6015", "KF-945A", "KF-6005", "KF-6009", "KF-6013", "KF-6019", "KF-6029", "KF-6017", "KF-6043", "KF-353A", "KF-354A" and "KF-355A" (all available from Shin-Etsu Chemical Co., Ltd.); and "FZ-2404", "SS-2805", "FZ-2411", "FZ-2412", "SH3771M", "SH3772M", "SH3773M", "SH3775M", "SH3749", "SS-280X Series", "BY22-008M", "BY11-030" and "BY25-337" (all available from Dow Corning Toray Co., Ltd.).

The amino-modified silicones are preferably those described under the name of "Amodimethicone" having an average molecular weight of about 3,000 to about 100,000 in CTFA Dictionary (US, Cosmetic Ingredient Dictionary), 3rd Edition. Examples of commercially available products of the amino-modified silicones include "SM 8704C" (available from Dow Corning Toray Co., Ltd.), "DC 929" (available from Dow Corning Corp.), "KT 1989" (available from GE Toshiba Silicone Co., Ltd.), and "8500 Conditioning Agent", "DOW CORNING TORAY SS-3588" and "DOW CORNING TORAY SILSTYLE 104" (all available from Dow Corning Toray Co., Ltd.).

The content of the silicones (except for the component (A) of the present invention) in the hair cosmetic of the present invention preferably from 0.05 to 20% by mass, more preferably from 0.1 to 10% by mass, and still more preferably from 0.5 to 5% by mass, from the viewpoints of smooth combing of fingers through hair and a less sticky feeing.

(Surfactant)

The hair cosmetic of the present invention may also contain a surfactant from the viewpoints of improving a stability of the system including a solubilizability or a dispersibility of the oil agent, etc., and enhancing a touch feeling of hair. As the surfactant, there may be used any of a cationic surfactant, a nonionic surfactant, an amphoteric surfactant and an anionic surfactant.

As the cationic surfactant, there may be mentioned an ammonium salt or a quaternary ammonium salt represented by the following general formula (13);

(13)

wherein $R^{46}$ and $R^{47}$ are each independently a hydrogen atom, an alkyl group having 1 to 28 carbon atoms or a benzyl group except for the case where $R^{46}$ and $R^{47}$ are constituted of a hydrogen atom, a benzyl group or a lower alkyl group having 1 to 3 carbon atoms, or a combination thereof, at the same time; $X^{3-}$ is a counter ion of the ammonium or quaternary ammonium.

In the general formula (13), one of $R^{46}$ and $R^{47}$ is preferably an alkyl group having 16 to 24 carbon atoms, more preferably an alkyl group having 22 carbon atoms, and still more preferably a straight-chain alkyl group having 22 carbon atoms, and the other of $R^{46}$ and $R^{47}$ is preferably a lower alkyl group having 1 to 3 carbon atoms, and more preferably a methyl group. Examples of $X^{3-}$ include an ethylsulfuric acid ion, a methylsulfuric acid ion, a chloride ion, an iodide ion, a sulfuric acid ion, a p-toluenesulfonic acid ion and a perchloric acid ion.

The cationic surfactant is preferably a mono-long chain alkyl quaternary ammonium salt. Specific examples of the cationic surfactant include cetyl trimethyl ammonium chloride, stearyl trimethyl ammonium chloride, alkyl trimethyl ammonium chlorides, behenyl trimethyl ammonium chloride and alkyl benzalkonium chlorides. Of these cationic surfactants, preferred are stearyl trimethyl ammonium chloride and behenyl trimethyl ammonium chloride.

Examples of the nonionic surfactant include polyoxyalkylene alkyl ethers, polyoxyalkylene alkenyl ethers, higher fatty acid sucrose esters, polyglycerin fatty acid esters, higher fatty acid mono- or diethanol amides, polyoxyethylene hardened castor oil, polyoxyethylene sorbitan fatty acid esters, polyoxyethylene sorbitol fatty acid esters, alkyl saccharide-based surfactants, alkyl amine oxides and alkyl amide amine oxides. Of these nonionic surfactants, preferred are polyoxyalkylene alkyl ethers and polyoxyethylene hardened castor oil, and more preferred are polyoxyethylene alkyl ethers and polyoxyethylene/polyoxypropylene alkyl ethers.

Examples of the amphoteric surfactant include imidazoline-based surfactants, carbobetaine-based surfactants, amide betaine-based surfactants, sulfobetaine-based surfactants, hydroxysulfobetaine-based surfactants and amide sulfobetaine-based surfactants. Of these amphoteric surfactants, preferred are betaine-based surfactants such as alkyl dimethyl aminoacetic acid betaines and fatty acid amide propyl betaines, and more preferred are fatty acid amide propyl betaines. The fatty acid amide propyl betaines are preferably those containing an acyl group having 8 to 18 carbon atoms, more preferably those containing an acyl group having 10 to 16 carbon atoms, and still more preferably lauric acid amide propyl betaine, palm kernel oil fatty acid amide propyl betaine and coconut oil fatty acid amide propyl betaine.

Examples of the anionic surfactant include alkyl benzenesulfonic acid salts, alkyl or alkenyl ether sulfuric acid salts, alkyl or alkenyl sulfuric acid salts, olefin sulfonic acid salts, alkane sulfonic acid salts, saturated or unsaturated fatty acid salts, alkyl or alkenyl ether carboxylic acid salts, α-sulfone fatty acid salts, N-acyl amino acid-type surfactants, phosphoric acid mono- or diester-type surfactants and sulfosuccinic acid esters. Examples of counter ions to an anion residue of the above surfactants include alkali metal ions such as a sodium ion and a potassium ion; alkali earth metal ions such as a calcium ion and a magnesium ion; an ammonium ion; alkanol amines containing 1 to 3 alkanol groups each having 2 or 3 carbon atoms (for example, monoethanol amine, diethanol amine, triethanol amine, triisopropanol amine, etc.).

Of these surfactants, from the viewpoint of a good touch feeling of hair upon using the hair cosmetic of the present invention, preferred are the cationic surfactant and the nonionic surfactant. These surfactants may be used alone or in combination of any two or more kinds thereof.

The content of the surfactant in the hair cosmetic is preferably from 0.01 to 10% by mass, and more preferably from 0.05 to 5% by mass, from the viewpoints of a good touch feeling of hair upon using the hair cosmetic of the present invention and a good stability of the system including solubilization, emulsification, etc., of organic solvents or oil agents upon formulating the organic solvents or oil agents in the hair cosmetic.

(Polyhydric Alcohol)

Further, the hair cosmetic used in the present invention may also contain a polyhydric alcohol other than the component (B). The polyhydric alcohol contributes to solubilization and stable dispersion of the component (B), and also acts synergistically with the component (B) to promote enhancement in hair luster or hair modifying effect. Examples of the polyhydric alcohol include glycerin, sorbitol, etc. Of these polyhydric alcohols, preferred is glycerin.

The polyhydric alcohols may be used alone or in combination of any two or more thereof.

The content of the polyhydric alcohol in the hair cosmetic is preferably from 0.1 to 10% by mass, and more preferably from 0.5 to 5% by mass.

(Other Components)

In addition to the aforementioned components, other components that can be used in ordinary hair cosmetics may also be appropriately formulated in the hair cosmetic of the present invention according to objects, applications, dosage forms, etc. Examples of the other components include anti-dandruff agents such as zinc pyrithione and octopirox; vitamin reagents; bactericides such as triclosan and triclocarban; anti-inflammatory agents such as dipotassium glycyrrhizate and tocopherol acetate; antiseptic agents such as methyl paraben and butyl paraben; chelating agents; humectants such as panthenol; colorants such as dyes and pigments; viscosity modifiers such as hydroxyethyl cellulose, methyl cellulose, polyethylene glycol and clay minerals; pH controllers such as organic acids, sodium hydroxide and potassium hydroxide; plant essences; pearling agents; perfumes; coloring matters; ultraviolet absorbers; antioxidants; and other components as described in "Encyclopedia of Shampoo Ingredients" (MICELLE PRESS).

(Configuration of Hair Cosmetic)

The hair cosmetic used in the present invention may be prepared with various configurations or dosage forms by ordinary methods. Examples of the configurations or dosage forms of the hair cosmetic include not only a liquid composition such as a mist, a lotion and a tonic, but also a semi-solid composition such as a gel, a paste, a cream and a wax.

The hair cosmetic of the present invention may also contain a propellant, and may be used in the form of an aerosol type hair cosmetic. The propellant contained in the hair cosmetic is not particularly limited as long as it can be usually used in the aerosol type hair cosmetic. Examples of the propellant usable in the present invention include lower saturated hydrocarbons such as propane, butane or mixtures thereof (including liquefied petroleum gases); ethers such as dimethyl ether; and a nitrogen gas, a carbon dioxide gas and a nitrous oxide gas. These propellants may be used alone or in combination of any two or more thereof.

The content of the propellant in the hair cosmetic of the present invention is preferably from 0.01 to 100% by mass, and more preferably from 10 to 40% by mass, on the basis of a total mass of the hair cosmetic (except for the propellant).

Furthermore, the hair cosmetic of the present invention may also be used in the form of a non-aerosol type hair cosmetic by filling a composition containing the organopolysiloxane as the component (A) into a foam injection container. The foam injection container is not particularly limited as long as it is capable of mixing the composition with air and injecting the resulting mixture in a foamed state therefrom. Examples of the foam injection container include a squeeze foamer that is used by pressing a barrel of a soft container with hand or fingers, a pump foamer that is used by pressing a head of a cap equipped with a pump mechanism with hand or fingers, a trigger type foamer, etc.

As the squeeze foamer, there may be mentioned those squeeze foamers described in JUM 62-042785B, JUM 62-042786B and JUM 62-042787B, and similar products thereto. As the pump foamer, there may be mentioned those pump foamers described in JP 7-315463A, JP 08-230961A, etc., and similar products thereto. These containers may be frequently provided at an injection portion thereof with a screen for the purpose of improving a quality of injected foam. Of these containers, preferred are those containers equipped with one or more screens having an opening size of from 100 to 300 mesh.

The hair cosmetic is preferably used in the form of a hair styling agent, a hair conditioning agent, etc. Examples of the preferred configurations or dosage forms of the hair cosmetic include a pump spray, an aerosol spray, a pump foam, an aerosol foam, a gel, a lotion, a mist and a cream. Of these configurations or dosage forms, preferred are a pump spray, a pump foam and an aerosol foam.

With respect to the aforementioned embodiments of the present invention, there are further described the following aspects concerning the organopolysiloxane graft polymer as well as the hair cosmetic containing the organopolysiloxane graft polymer.

<1> An organopolysiloxane graft polymer including an organopolysiloxane segment as a main chain thereof and an unsaturated monomer-derived polymer segment as a side chain thereof, in which a content of the organopolysiloxane segment in the organopolysiloxane graft polymer is not less than 35% by mass, preferably not less than 40% by mass, and more preferably not less than 45% by mass, and is also not more than 70% by mass, preferably not more than 65% by mass, and more preferably not more than 60% by mass; and the unsaturated monomer-derived polymer segment contains a repeating unit derived from a nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from a cationic unsaturated monomer in an amount of not less than 10% by mass and not more than 60% by mass.

<2> The organopolysiloxane graft polymer according to the above aspect <1>, wherein a weight-average molecular weight of the organopolysiloxane segment is not less than 5,000, preferably not less than 10,000, and more preferably not less than 20,000, and is also not more than 200,000, preferably not more than 150,000, more preferably not more than 100,000, and still more preferably not more than 60,000.

<3> The organopolysiloxane graft polymer according to the above aspect <1> or <2>, wherein a number-average molecular weight (MNg) of the organopolysiloxane segment being present between the adjacent unsaturated monomer-derived polymer segments among the organopolysiloxane segments is not less than 500, preferably not less than 700, more preferably not less than 1,000, and still more preferably not less than 1,500, and is also not more than 20,000, preferably not more than 10,000, more preferably not more than 4,000, and still more preferably not more than 3,000.

<4> The organopolysiloxane graft polymer according to any one of the above aspects <1> to <3>, wherein the organopolysiloxane segment is a modified organopolysiloxane segment represented by the following formula (1) or (2):

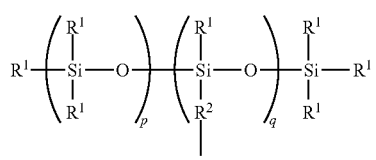 (1)

-continued

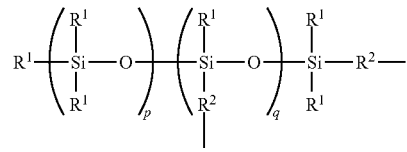 (2)

wherein $R^1$ groups are each independently an alkyl group having not less than 1 and not more than 22 carbon atoms or an aryl group having not less than 6 and not more than 14 carbon atoms; $R^2$ is an alkylene group that may contain a hetero atom; p is a number of not less than 2 and not more than 4,000; and q is a number of not less than 2 and not more than 500, in which repeating units in the number of p and repeating units in the number of q may be bonded to each other either in a block form or in a random form.

<5> The organopolysiloxane graft polymer according to the above aspect <4>, wherein in the above general formulae (1) and (2), $R^1$ is a straight-chain or branched-chain alkyl group having 1 to 6 carbon atoms, preferably a straight-chain or branched-chain alkyl group having 1 to 3 carbon atoms, and more preferably a methyl group.

<6> The organopolysiloxane graft polymer according to the above aspect <4> or <5>, wherein in the above general formulae (1) and (2), p is a number of not less than 50, preferably not less than 100, and more preferably not less than 150, and is also a number of not more than 2,000, preferably not more than 1,500, and more preferably not more than 1,000.

<7> The organopolysiloxane graft polymer according to any one of the above aspects <4> to <6>, wherein in the above general formulae (1) and (2), q is a number of not less than 3, and preferably not less than 5, and is also a number of not more than 50, and preferably not more than 30.

<8> The organopolysiloxane graft polymer according to any one of the above aspects <4> to <7>, wherein in the above general formulae (1) and (2), the number of carbon atoms of the alkylene group ($R^2$) which may contain a hetero atom is not less than 2, and preferably not less than 3, and is also not more than 20, preferably not more than 15, more preferably not more than 10, and still more preferably not more than 8.

<9> The organopolysiloxane graft polymer according to any one of the above aspects <4> to <8>, wherein in the above general formulae (1) and (2), the alkylene group ($R^2$) which may contain a hetero atom is bonded to the unsaturated monomer-derived polymer segment through the hetero atom, preferably through a nitrogen atom, an oxygen atom or a sulfur atom, and more preferably through a sulfur atom.

<10> The organopolysiloxane graft polymer according to any one of the above aspects <4> to <9>, wherein in the above general formulae (1) and (2), the alkylene group ($R^2$) which may contain a hetero atom is a group selected from the group consisting of those groups represented by the following formulae (i) to (xii), preferably a group selected from the group consisting of those groups represented by the following formulae (xi) and (xii), and more preferably a group represented by the following formula (xii):

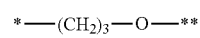 (i)

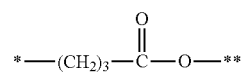 (ii)

-continued

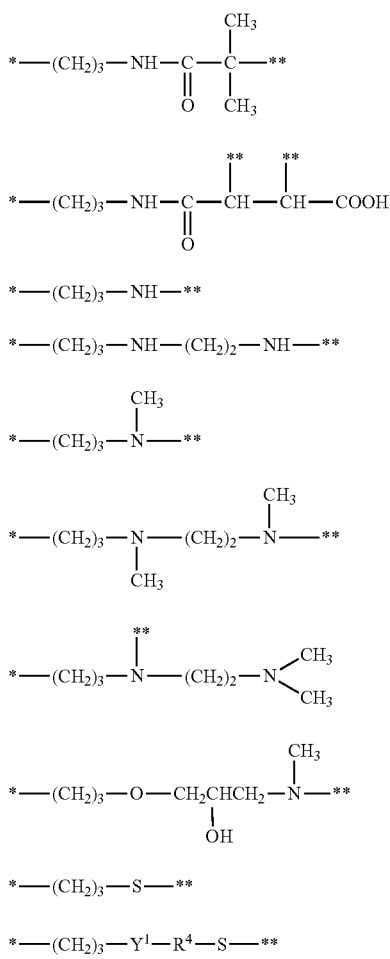

(iii)
(iv)
(v)
(vi)
(vii)
(viii)
(ix)
(x)
(xi)
(xii)

wherein "*" represents a moiety bonded to the silicon atom in the general formula (1) or (2), and "**" represents a moiety bonded to the unsaturated monomer-derived polymer segment;

in the formula (xii), $Y^1$ is an atom or group selected from the group consisting of —O—, —OCO—, —COO—, —CONH— and —NHCO—; and in the formula (xii), $R^4$ is an alkylene group that may be substituted with at least one substituent group selected from the group consisting of a hydroxy group, an amino group, a $(C_1-C_3)$ alkyl amino group, a di-$(C_1-C_3)$ alkyl amino group, an amide group obtained by dehydration condensation of an amino group and a fatty acid having 2 to 4 carbon atoms, and a $(C_1-C_3)$ alkyl ester group.

<11> The organopolysiloxane graft polymer according to the above aspect <10>, wherein in the formula (xii), $Y^1$ is —CONH— or —NHCO—, and preferably —NHCO—.

<12> The organopolysiloxane graft polymer according to the above aspect <10> or <11>, wherein in the formula (xii), $R^4$ is an alkylene group that may be substituted with an acetamide group, a $(C_1-C_3)$ alkyl amino group or an amino group.

<13> The organopolysiloxane graft polymer according to any one of the above aspects <10> to <12>, wherein in the formula (xii), $R^4$ is a group selected from the group consisting of those groups represented by the following formulae (xiii) to (xv):

—(CH$_2$)$_n$— (xiii)

n = 2~4

$$—\overset{H}{\underset{\underset{NH_3X^{1-}}{|}}{C}}—(CH_2)_2—$$ (xiv)

$$—\overset{H}{\underset{\underset{\underset{\underset{CH_3}{|}}{\underset{C=O}{|}}}{\underset{NH}{|}}}{C}}—(CH_2)_2—$$ (xv)

wherein $X^{1-}$ in the formula (xiv) is an anion.

<14> The organopolysiloxane graft polymer according to any one of the above aspects <1> to <13>, wherein a content of the repeating unit derived from the nonionic unsaturated monomer having a glass transition temperature Tg of 60° C. or higher (except for a repeating unit derived from an unsaturated monomer containing an amino group) in the unsaturated monomer-derived polymer segment is not less than 45% by mass, and preferably not less than 50% by mass, and is also not more than 85% by mass, and preferably not more than 80% by mass.

<15> The organopolysiloxane graft polymer according to any one of the above aspects <1> to <14>, wherein Tg of the nonionic monomer is preferably not lower than 80° C., more preferably not lower than 100° C., and still more preferably not lower than 110° C., and is also preferably not higher than 190° C., more preferably not higher than 170° C., and still more preferably not higher than 150° C.

<16> The organopolysiloxane graft polymer according to any one of the above aspects <1> to <15>, wherein the repeating unit derived from the nonionic unsaturated monomer is a repeating unit derived from at least one unsaturated monomer selected from the group consisting of tert-butyl acrylate, acrylamide, N-sec-butyl acrylamide, N-tert-butyl acrylamide, N,N-dibutyl acrylamide, N,N-diisopropyl acrylamide, N,N-dimethyl acrylamide, isohexyl acrylamide, isooctyl acrylamide, N-(1-methylbutyl)acrylamide, sec-butyl methacrylate, tert-butyl methacrylate and N-tert-butyl methacrylamide; preferably a repeating unit derived from at least one unsaturated monomer selected from the group consisting of tert-butyl acrylate, N-tert-butyl acrylamide, tert-butyl methacrylate and N-tert-butyl methacrylamide; and more preferably a repeating unit derived from N-tert-butyl acrylamide.

<17> The organopolysiloxane graft polymer according to any one of the above aspects <1> to <16>, wherein a content of the repeating unit derived from the cationic unsaturated monomer in the unsaturated monomer-derived polymer segment is not less than 15% by mass, and preferably not less than 20% by mass, and is also not more than 55% by mass, and preferably not more than 50% by mass.

<18> The organopolysiloxane graft polymer according to any one of the above aspects <1> to <17>, wherein the repeating unit derived from the cationic unsaturated monomer is a repeating unit derived from a compound represented by the following general formula (3):

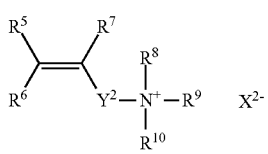
(3)

wherein $R^5$, $R^6$ and $R^7$ are each independently a hydrogen atom or a methyl group; $R^8$, $R^9$ and $R^{10}$ are each independently a hydrogen atom or an alkyl group having 1 to 3 carbon atoms; $Y^2$ is a group selected from the group consisting of an alkylene group having 1 to 12 carbon atoms, —COOR$^{11}$—, —CONHR$^{11}$—, —OCOR$^{11}$— and —R$^{12}$—OCO—R$^{11}$— wherein $R^{11}$ and $R^{12}$ are each independently an alkylene group having 1 to 5 carbon atoms; and $X^{2-}$ is an anion.

<19> The organopolysiloxane graft polymer according to the above aspect <18>, wherein in the above general formula (3), $R^5$ and $R^6$ are each a hydrogen atom.

<20> The organopolysiloxane graft polymer according to the above aspect <18> or <19>, wherein in the above general formula (3), $R^8$ and $R^9$ are each a methyl group or an ethyl group.

<21> The organopolysiloxane graft polymer according to any one of the above aspects <18> to <20>, wherein in the above general formula (3), $R^{10}$ is a hydrogen atom.

<22> The organopolysiloxane graft polymer according to any one of the above aspects <18> to <21>, wherein in the above general formula (3), $R^{11}$ is an alkylene group having 1 to 5 carbon atoms and preferably 2 to 3 carbon atoms.

<23> The organopolysiloxane graft polymer according to any one of the above aspects <18> to <22>, wherein in the above general formula (3), $R^{12}$ is a methylene group.

<24> The organopolysiloxane graft polymer according to any one of the above aspects <18> to <22>, wherein in the above general formula (3), $Y^2$ is —COOR$^{11}$— or —CONHR$^{11}$—.

<25> The organopolysiloxane graft polymer according to any one of the above aspects <18> to <24>, wherein in the above general formula (3), $X^{2-}$ is an anion selected from the group consisting of a halide ion and an organic acid ion; preferably an anion selected from the group consisting of a chloride ion, a bromide ion, an alkylsulfuric acid ion having not less than 1 and not more than 3 carbon atoms, a acetic acid ion, a lactic acid ion, a benzoic acid ion, an adipic acid ion, a formic acid ion, a malic acid ion and a glycolic acid ion; more preferably an anion selected from the group consisting of an alkylsulfuric acid ion having not less than 1 and not more than 3 carbon atoms, a lactic acid ion, a formic acid ion, a malic acid ion and a glycolic acid ion; and still more preferably a lactic acid ion.

<26> The organopolysiloxane graft polymer according to any one of the above aspects <1> to <25>, wherein a sum of contents of the repeating unit derived from the nonionic unsaturated monomer having Tg of 60° C. or higher and the repeating unit derived from the cationic unsaturated monomer in the unsaturated monomer-derived polymer segment as a side chain of the organopolysiloxane graft polymer is preferably not less than 70% by mass, more preferably not less than 80% by mass, still more preferably not less than 90% by mass, and even still more preferably not less than 95% by mass, and is also preferably not more than 100% by mass.

<27> The organopolysiloxane graft polymer according to any one of the above aspects <1> to <26>, wherein the organopolysiloxane graft polymer is produced by subjecting unsaturated monomers including the nonionic unsaturated monomer having a glass transition temperature Tg of 60° C. or higher and the cationic unsaturated monomer to polymerization in the presence of a radical-reactive organopolysiloxane.

<28> The organopolysiloxane graft polymer according to any one of the above aspects <1> to <27>, wherein the organopolysiloxane graft polymer is produced by subjecting unsaturated monomers including the nonionic unsaturated monomer having a glass transition temperature Tg of 60° C. or higher and the cationic unsaturated monomer to polymerization in the presence of a radical-reactive organopolysiloxane represented by the following general formula (5) or (6).

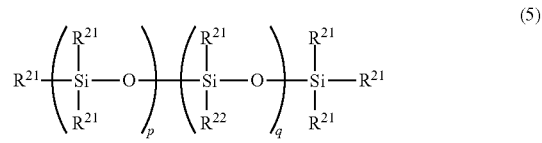
(5)

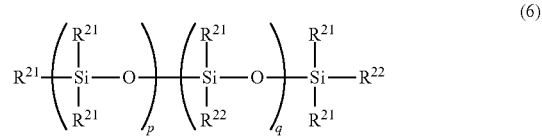
(6)

wherein $R^{21}$ groups are each independently an alkyl group having not less than 1 and not more than 22 carbon atoms or an aryl group having not less than 6 and not more than 14 carbon atoms; $R^{22}$ is an alkyl group containing a radical-reactive functional group; p is a number of not less than 2 and not more than 4,000; and q is a number of not less than 2 and not more than 500, in which repeating units in the number of p and repeating units in the number of q may be bonded to each other either in a block form or in a random form.

<29> The organopolysiloxane graft polymer according to the above aspect <28>, wherein in the above general formulae (5) and (6), $R^{21}$ is a straight-chain or branched-chain alkyl group having 1 to 6 carbon atoms, preferably a straight-chain or branched-chain alkyl group having 1 to 3 carbon atoms, and more preferably a methyl group.

<30> The organopolysiloxane graft polymer according to the above aspect <28> or <29>, wherein in the above general formulae (5) and (6), p is a number of not less than 50, preferably not less than 100, and more preferably not less than 150, and is also a number of not more than 2,000, preferably not more than 1,500, and more preferably not more than 1,000.

<31> The organopolysiloxane graft polymer according to any one of the above aspects <28> to <30>, wherein in the general formulae (5) and (6), q is a number of not less than 3, and preferably not less than 5, and is also a number of not more than 50, and preferably not more than 30.

<32> The organopolysiloxane graft polymer according to any one of the above aspects <28> to <31>, wherein the radical-reactive functional group is a group selected from the group consisting of an ethylenically unsaturated group, a halogen group and a sulfanyl group, and preferably a sulfanyl group.

<33> The organopolysiloxane graft polymer according to any one of the above aspects <28> to <32>, wherein in the general formulae (5) and (6), the number of carbon atoms of the radical-reactive group-containing alkyl group represented by $R^{22}$ is not less than 2, and preferably not less than 3, and is also not more than 20, preferably not more than 15, more preferably not more than 10, and still more preferably not more than 8.

<34> The organopolysiloxane graft polymer according to any one of the above aspects <28> to <33>, wherein in the general formulae (5) and (6), the radical-reactive group-containing alkyl group represented by $R^{22}$ may be substituted with at least one substituent group selected from the group consisting of a hydroxy group, an amino group, a $(C_1-C_3)$ alkyl amino group, a di-$(C_1-C_3)$ alkyl amino group, an amide group obtained by dehydration condensation of an amino group and a fatty acid having 2 to 4 carbon atoms, a carboxy group, and a $(C_1-C_3)$ alkyl ester group, and preferably with an acetamide group, a $(C_1-C_3)$ alkyl amino group or an amino group.

<35> The organopolysiloxane graft polymer according to any one of the above aspects <28> to <34>, wherein in the general formulae (5) and (6), the radical-reactive group-containing alkyl group represented by $R^{22}$ is interrupted by at least one atom or functional group selected from the group consisting of an oxygen atom, a sulfur atom, —NH—, —COO—, —NHCO— and —NR$^{23}$CO—, and preferably by —NHCO—, in which $R^{23}$ is an alkyl group having 1 to 3 carbon atoms.

<36> The organopolysiloxane graft polymer according to any one of the above aspects <28> to <35>, wherein in the general formulae (5) and (6), the radical-reactive group-containing alkyl group represented by $R^{22}$ is a group selected from the group consisting of those groups represented by the following formulae (xvii) to (xx), and preferably a group represented by the following formula (xix) or (xx):

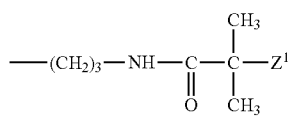

(xvii)

$Z^1 = Cl$ or Br

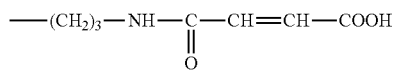

(xviii)

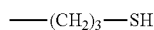

(xix)

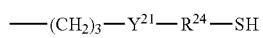

(xx)

wherein $Y^{21}$ in the formula (xx) is an atom or group selected from the group consisting of —O—, —OCO—, —COO—, —CONH—, and —NHCO—; and $R^{24}$ in the formula (xx) is an alkylene group that may be substituted with at least one substituent group selected from the group consisting of a hydroxy group, an amino group, a $(C_1-C_3)$ alkyl amino group, a di-$(C_1-C_3)$ alkyl amino group, an amide group obtained by dehydration condensation of an amino group and a fatty acid having 2 to 4 carbon atoms, and a $(C_1-C_3)$ alkyl ester group, and preferably an alkylene group that may be substituted with an acetamide group, a $(C_1-C_3)$ alkyl amino group or an amino group.

<37> The organopolysiloxane graft polymer according to any one of the above aspects <28> to <36>, wherein the number of moles of the radical-reactive functional group being present per a unit mass of the radical-reactive organopolysiloxane is not more than 1/500 mol/g, preferably not more than 1/700 mol/g, more preferably not more than 1/1,000 mol/g, and still more preferably not more than 1/1,500 mol/g, and is also not less than 1/10,000 mol/g, preferably not less than 1/5,000 mol/g, more preferably not less than 1/3,000 mol/g, and still more preferably not less than 1/2,500 mol/g.

<38> The organopolysiloxane graft polymer according to any one of the above aspects <27> to <37>, wherein the radical-reactive organopolysiloxane is produced by reacting a reactive functional group-containing organopolysiloxane with a radical reactivity-imparting agent.

<39> The organopolysiloxane graft polymer according to any one of the above aspects <27> to <38>, wherein the radical-reactive organopolysiloxane is produced by reacting a reactive functional group-containing organopolysiloxane represented by the following general formula (7) or (8) with a radical reactivity-imparting agent:

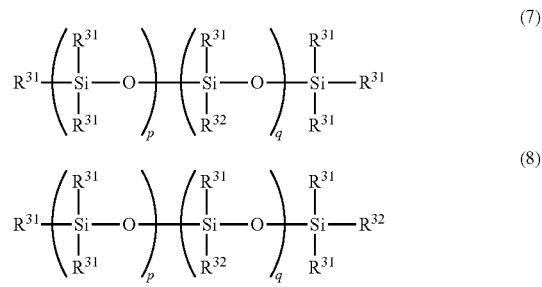

wherein $R^{31}$ groups are each independently an alkyl group having 1 to 22 carbon atoms or an aryl group having 6 to 14 carbon atoms; $R^{32}$ is an alkyl group containing a reactive functional group; p is a number of not less than 2 and not more than 4,000; and q is a number of not less than 2 and not more than 500, in which repeating units in the number of p and repeating units in the number of q may be bonded to each other either in a block form or in a random form.

<40> The organopolysiloxane graft polymer according to the above aspect <38> or <39>, wherein the reactive functional group is a group selected from the group consisting of a hydroxy group, an amino group, a carboxy group and an epoxy group.

<41> The organopolysiloxane graft polymer according to the above aspect <39> or <40>, wherein in the general formulae (7) and (8), the number of carbon atoms of the reactive group-containing alkyl group represented by $R^{32}$ is not less than 2, and preferably not less than 3, and is also not more than 15, preferably not more than 10, and more preferably not more than 5.

<42> The organopolysiloxane graft polymer according to any one of the above aspects <39> to <41>, wherein in the general formulae (7) and (8), the reactive group-containing alkyl group represented by $R^{32}$ is a group selected from the group consisting of those groups represented by the following formulae (xxi) to (xxviii), preferably a group selected from the group consisting of those groups represented by the following formulae (xxi) to (xxiv), and more preferably a group represented by the following formula (xxiv).

(xxi)

(xxii)

(xxiii)

(xxiv)

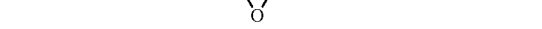

(xxv)

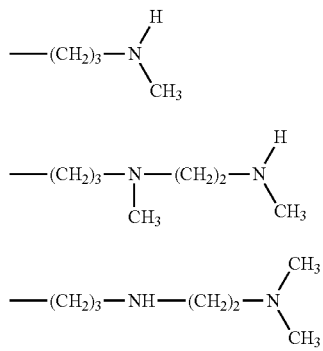

(xxvi), (xxvii), (xxviii)

<43> The organopolysiloxane graft polymer according to any one of the above aspects <38> to <42>, wherein a weight-average molecular weight of the reactive functional group-containing organopolysiloxane is not less than 3,000, preferably not less than 5,000, more preferably not less than 10,000, and still more preferably not less than 20,000, and is also not more than 200,000, preferably not more than 150,000, more preferably not more than 100,000, and still more preferably not more than 60,000.

<44> The organopolysiloxane graft polymer according to any one of the above aspects <38> to <43>, wherein the number of moles of the reactive functional group being present per a unit mass of the reactive functional group-containing organopolysiloxane is not more than 1/500 mol/g, preferably not more than 1/700 mol/g, more preferably not more than 1/1,000 mol/g, and still more preferably not more than 1/1,500 mol/g, and is also not less than 1/10,000 mol/g, preferably not less than 1/5,000 mol/g, more preferably not less than 1/3,000, and still more preferably not less than 1/2,500.

<45> The organopolysiloxane graft polymer according to any one of the above aspects <38> to <44>, wherein the radical reactivity-imparting agent is a compound containing at least one functional group selected from the group consisting of a carboxy group, an ester group, an epoxy group, a hydroxy group and lactones, and a radical-reactive functional group, in a molecule thereof, or an unsubstituted or substituted thiolactone.

<46> The organopolysiloxane graft polymer according to the above aspect <45>, wherein the radical-reactive functional group of the radical reactivity-imparting agent is a group selected from the group consisting of an ethylenically unsaturated group, a halogeno group and a sulfanyl group, and preferably a sulfanyl group.

<47> The organopolysiloxane graft polymer according to any one of the above aspects <38> to <46>, wherein the radical reactivity-imparting agent is at least one compound selected from the group consisting of 3-mercapto propionic acid, γ-butyrolactone thiol, γ-thiobutyrolactone, N-acetyl-DL-homocysteine thiolactone and DL-homocysteine thiolactone hydrochloride, and preferably N-acetyl-DL-homocysteine thiolactone.

<48> The organopolysiloxane graft polymer according to any one of the above aspects <38> to <47>, wherein an amount of the radical reactivity-imparting agent used is not less than 0.8 equivalent, preferably not less than 0.9 equivalent, and more preferably not less than 0.95 equivalent, and is also not more than 1.2 equivalent, preferably not more than 1.1 equivalent, and more preferably not more than 1.05 equivalent, on the basis of a total amount of the reactive functional group of the reactive functional group-containing organopolysiloxane.

<49> The organopolysiloxane graft polymer according to any one of the above aspects <27> to <48>, wherein an amount of the unsaturated monomers used is not less than 30% by mass, and preferably not less than 40% by mass, and is also not more than 65% by mass, preferably not more than 60% by mass, and more preferably not more than 55% by mass, on the basis of a total amount of the radical-reactive organopolysiloxane and the unsaturated monomers.

<50> The organopolysiloxane graft polymer according to any one of the above aspects <27> to <49>, wherein a content of the nonionic unsaturated monomer having Tg of 60° C. or higher (except for an unsaturated monomer containing an amino group) in the unsaturated monomers is not less than 40% by mass, preferably not less than 45% by mass, and more preferably not less than 50% by mass, and is also not more than 90% by mass, preferably not more than 85% by mass, and more preferably not more than 80% by mass, on the basis of a total amount of the whole unsaturated monomers.

<51> The organopolysiloxane graft polymer according to any one of the above aspects <27> to <50>, wherein Tg of the nonionic monomer is preferably not lower than 80° C., more preferably not lower than 100° C., and still more preferably not lower than 110° C., and is also preferably not higher than 190° C., more preferably not higher than 170° C., and still more preferably not higher than 150° C.

<52> The organopolysiloxane graft polymer according to any one of the above aspects <27> to <51>, wherein the nonionic unsaturated monomer is at least one unsaturated monomer selected from the group consisting of tert-butyl acrylate, acrylamide, N-sec-butyl acrylamide, N-tert-butyl acrylamide, N,N-dibutyl acrylamide, N,N-diisopropyl acrylamide, N,N-dimethyl acrylamide, isohexyl acrylamide, isooctyl acrylamide, N-(1-methylbutyl)acrylamide, sec-butyl methacrylate, tert-butyl methacrylate and N-tert-butyl methacrylamide; preferably at least one unsaturated monomer selected from the group consisting of tert-butyl acrylate, N-tert-butyl acrylamide, tert-butyl methacrylate and N-tert-butyl methacrylamide; and more preferably N-tert-butyl acrylamide.

<53> The organopolysiloxane graft polymer according to any one of the above aspects <27> to <52>, wherein a content of the cationic unsaturated monomer in the unsaturated monomers is not less than 10% by mass, preferably not less than 15% by mass, and more preferably not less than 20% by mass, and is also not more than 60% by mass, preferably not more than 55% by mass, and more preferably not more than 50% by mass, on the basis of a total amount of the whole unsaturated monomers.

<54> The organopolysiloxane graft polymer according to any one of the above aspects <27> to <53>, wherein the cationic unsaturated monomer is a compound represented by the general formula (3) described in the above aspect <18>.

<55> The organopolysiloxane graft polymer according to the above aspect <54>, wherein in the above general formula (3), $R^5$ and $R^6$ are each a hydrogen atom.

<56> The organopolysiloxane graft polymer according to the above aspect <54> or <55>, wherein in the above general formula (3), $R^8$ and $R^9$ are each a methyl group.

<57> The organopolysiloxane graft polymer according to any one of the above aspects <54> to <56>, wherein in the above general formula (3), $R^{10}$ is a hydrogen atom.

<58> The organopolysiloxane graft polymer according to any one of the above aspects <54> to <57>, wherein in the above general formula (3), $R^{11}$ is an alkylene group having 1 to 5 carbon atoms and preferably 2 to 3 carbon atoms.

<59> The organopolysiloxane graft polymer according to any one of the above aspects <54> to <58>, wherein in the above general formula (3), $R^{12}$ is a methylene group.

<60> The organopolysiloxane graft polymer according to any one of the above aspects <54> to <59>, wherein in the above general formula (3), $Y^2$ is —COOR$^{11}$— or —CONHR$^{11}$—.

<61> The organopolysiloxane graft polymer according to any one of the above aspects <54> to <60>, wherein in the above general formula (3), $X^{2-}$ is an anion selected from the group consisting of a halide ion and an organic acid ion; preferably an anion selected from the group consisting of a chloride ion, a bromide ion, an alkylsulfuric acid ion having not less than 1 and not more than 3 carbon atoms, a acetic acid ion, a lactic acid ion, a benzoic acid ion, an adipic acid ion, a formic acid ion, a malic acid ion and a glycolic acid ion; more preferably an anion selected from the group consisting of an alkylsulfuric acid ion having not less than 1 and not more than 3 carbon atoms, a lactic acid ion, a formic acid ion, a malic acid ion and a glycolic acid ion; and still more preferably a lactic acid ion.

<62> The organopolysiloxane graft polymer according to any one of the above aspects <27> to <61>, wherein a sum of contents of the nonionic unsaturated monomer having Tg of 60° C. or higher and the cationic unsaturated monomer in the unsaturated monomers is not less than 70% by mass, preferably not less than 80% by mass, more preferably not less than 90% by mass, and still more preferably not less than 95% by mass, and is also not more than 100% by mass.

<63> The organopolysiloxane graft polymer according to any one of the above aspects <27> to <62>, wherein the polymerization is a solution polymerization that is carried out in the presence of a solvent.

<64> The organopolysiloxane graft polymer according to the above aspect <63>, wherein the solvent is at least one solvent selected from the group consisting of an alcohol having not less than 1 and not more than 8 carbon atoms, an ester having not less than 2 and not more than 8 carbon atoms and an ether having not less than 2 and not more than 8 carbon atoms; and preferably at least one solvent selected from the group consisting of water and an alcohol having not less than 1 and not more than 3 carbon atoms.

<65> The organopolysiloxane graft polymer according to the above aspect <63> or <64>, wherein an amount of the solvent used is not less than 60% by mass, preferably not less than 80% by mass, and more preferably not less than 100% by mass, and is also not more than 900% by mass, preferably not more than 400% by mass, more preferably not more than 200% by mass, and still more preferably not more than 150% by mass, on the basis of a total amount of the radical-reactive organopolysiloxane and the unsaturated monomers.

<66> The organopolysiloxane graft polymer according to any one of the above aspects <27> to <65>, wherein the polymerization is carried out in the presence of a polymerization initiator; preferably a polymerization initiator selected from the group consisting of azo-based initiators, peroxide-based initiators and persulfate-based initiators; more preferably a polymerization initiator selected from the group consisting of 2,2'-azobisisobutyronitrile, 2,2'-azobis(2,4-dimethyl valeronitrile), lauroyl peroxide, benzoyl peroxide and ammonium persulfate; and still more preferably 2,2'-azobis(2,4-dimethyl valeronitrile).

<67> The organopolysiloxane graft polymer according to the above aspect <66>, wherein an amount of the polymerization initiator used is not less than 0.01% by mass, preferably not less than 0.1% by mass, and more preferably not less than 0.5% by mass, and is also not more than 10% by mass, preferably not more than 5% by mass, and more preferably not more than 2% by mass, on the basis of a total amount of the unsaturated monomers used.

<68> The organopolysiloxane graft polymer according to any one of the above aspects <27> to <67>, wherein the polymerization is carried out at a temperature of not lower than 50° C., and preferably not lower than 60° C., and also not higher than 120° C., preferably not higher than 100° C., more preferably not higher than 90° C. and still more preferably not higher than 80° C.

<69> The organopolysiloxane graft polymer according to any one of the above aspects <27> to <68>, wherein the polymerization is carried out until a conversion rate of the unsaturated monomers reaches not less than 80%, and preferably not less than 90% and not more than 100%.

<70> The organopolysiloxane graft polymer according to any one of the above aspects <27> to <69>, wherein the polymerization is carried out for a time period of not less than 0.1 h, preferably not less than 0.5 h, and more preferably not less than 1 h, and also not more than 60 h, preferably not more than 30 h, more preferably not more than 20 h, and still more preferably not more than 10 h.

<71> A process for producing the organopolysiloxane graft polymer according to any one of the above aspects <1> to <70>, comprising the step of polymerizing the unsaturated monomers including the nonionic unsaturated monomer having a glass transition temperature Tg of 60° C. or higher and the cationic unsaturated monomer in the presence of the radical-reactive organopolysiloxane.

<72> The process for producing the organopolysiloxane graft polymer according to the above aspect <71>, wherein the radical-reactive organopolysiloxane is produced by reacting the reactive functional group-containing organopolysiloxane with the radical reactivity-imparting agent.

<73> A process for producing an organopolysiloxane graft polymer including an organopolysiloxane segment as a main chain thereof and an unsaturated monomer-derived polymer segment as a side chain thereof, said process including the step of polymerizing unsaturated monomers including a nonionic unsaturated monomer having a glass transition temperature Tg of 60° C. or higher and a cationic unsaturated monomer in the presence of a radical-reactive organopolysiloxane represented by the following general formula (5) or (6):

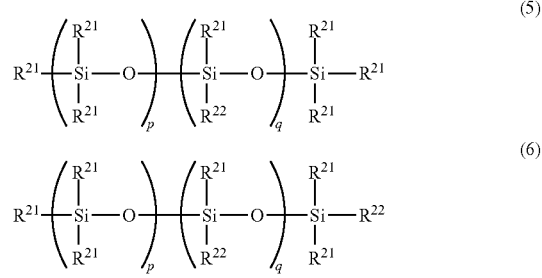

wherein $R^{21}$ groups are each independently an alkyl group having not less than 1 and not more than 22 carbon atoms or an aryl group having not less than 6 and not more than 14 carbon atoms; $R^{22}$ is an alkyl group containing a radical-reactive functional group; p is a number of not less than 2 and not more than 4,000; and q is a number of not less than 2 and not more than 500, in which repeating units in the number of p and repeating units in the number of q may be bonded to each other either in a block form or in a random form, in which a content of the organopolysiloxane segment in the organopolysiloxane graft polymer is not less than 35% by mass and not more than 70% by mass; and a content of a repeating unit derived from the nonionic unsaturated monomer having a glass transition temperature Tg of 60° C. or higher (except for a repeating unit derived from an unsaturated monomer containing an amino group) in the unsaturated monomer-derived polymer segment is not less than 40% by mass and not more than 90% by mass, and a content of a repeating unit derived from the cationic unsaturated monomer in the unsaturated monomer-derived polymer segment is not less than 10% by mass and not more than 60% by mass.

<74> The process for producing an organopolysiloxane graft polymer according to the above aspect <73>, wherein the radical-reactive functional group is a group selected from the group consisting of an ethylenically unsaturated group, a halogeno group and a sulfanyl group, and preferably a sulfanyl group.

<75> The process for producing an organopolysiloxane graft polymer according to the above aspect <73> or <74>, wherein in the general formulae (5) and (6), the number of carbon atoms of the radical-reactive group-containing alkyl group represented by $R^{22}$ is not less than 2, and preferably not less than 3, and is also not more than 20, preferably not more than 15, more preferably not more than 10, and still more preferably not more than 8.

<76> The process for producing an organopolysiloxane graft polymer according to any one of the above aspects <73> to <75>, wherein a weight-average molecular weight of the radical-reactive organopolysiloxane is preferably not less than 5,000, more preferably not less than 10,000, and still more preferably not less than 20,000, and is also preferably not more than 200,000, more preferably not more than 150,000, still more preferably not more than 100,000, and even still more preferably not more than 60,000.

<77> The process for producing an organopolysiloxane graft polymer according to any one of the above aspects <73> to <76>, wherein the number of moles of the radical-reactive functional group being present per a unit mass of the radical-reactive organopolysiloxane is not more than 1/500 mol/g, preferably not more than 1/700 mol/g, more preferably not more than 1/1,000 mol/g, and still more preferably not more than 1/1,500 mol/g, and is also not less than 1/10,000 mol/g, preferably not less than 1/5,000 mol/g, more preferably not less than 1/3,000, and still more preferably not less than 1/2,500 mol/g.

<78> The process for producing an organopolysiloxane graft polymer according to any one of the above aspects <73> to <77>, wherein a sum of contents of the nonionic unsaturated monomer having Tg of 60° C. or higher and the cationic unsaturated monomer in the unsaturated monomers is preferably not less than 70% by mass, more preferably not less than 80% by mass, still more preferably not less than 90% by mass, and even still more preferably not less than 95% by mass, and is also preferably not more than 100% by mass.

<79> The process for producing an organopolysiloxane graft polymer according to any one of the above aspects <73> to <78>, wherein the radical-reactive organopolysiloxane is produced by reacting a reactive functional group-containing organopolysiloxane represented by the following general formula (7) or (8) with a radical reactivity-imparting agent:

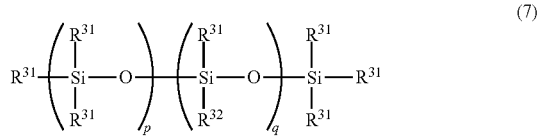

(7)

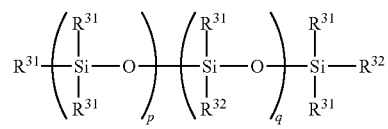

(8)

wherein $R^{31}$ groups are each independently an alkyl group having 1 to 22 carbon atoms or an aryl group having 6 to 14 carbon atoms; $R^{32}$ is an alkyl group containing a reactive functional group; p is a number of not less than 2 and not more than 4,000; and q is a number of not less than 2 and not more than 500, in which repeating units in the number of p and repeating units in the number of q may be bonded to each other either in a block form or in a random form.

<80> The process for producing an organopolysiloxane graft polymer according to any one of the above aspects <73> to <79>, wherein the reactive functional group is a group selected from the group consisting of a hydroxy group, an amino group, a carboxy group and an epoxy group.

<81> A hair cosmetic including the organopolysiloxane graft polymer according to any one of the above aspects <1> to <70>.

<82> A use of the organopolysiloxane graft polymer according to any one of the above aspects <1> to <70>, for a hair cosmetic.

<83> A hairdressing method including the step of applying the organopolysiloxane graft polymer according to any one of the above aspects <1> to <70> to hair.

EXAMPLES

In the following Examples, etc., "%" indicates "% by mass", unless otherwise specified.

<GPC Measuring Conditions of Weight-Average Molecular Weight (MWsim) of Reactive Functional Group-Containing Organopolysiloxane and Weight-Average Molecular Weight (MWra) of Radical-Reactive Organopolysiloxane)

Column: "K-804L" (available from Tosoh Corp.); Two columns connected in series were used.

Eluent 1 mM Dimethyl dodecyl amine/chloroform solution

Flow Rate: 1.0 mL/min

Column Temperature: 40° C.

Detector: RI

Sample: 5 mg/mL; 500 μL

Under the above measuring conditions, the weight-average molecular weights were measured in terms of a polystyrene as a reference standard substance.

<Calculation of Number of Moles of Sulfanyl Group Per Unit Mass of Sulfanyl Group-Modified Organopolysiloxane (Radical-Reactive Organopolysiloxane) Synthesized from Side-Chain Primary Aminopropyl-Modified Organopolysiloxane (Reactive Functional Group-Containing Organopolysiloxane)>

The amount of an amino group contained in a mixture of a side-chain primary aminopropyl-modified organopolysiloxane (reactive functional group-containing organopolysiloxane) and a sulfanyl group-modified organopolysiloxane (radical-reactive organopolysiloxane) obtained by the reaction between the side-chain primary aminopropyl-modified organopolysiloxane and N-acetyl-DL-homocysteine thiolactone (radical reactivity-imparting agent) was measured to determine an amount of the amino group consumed by the reaction. The measurement of the amount of the amino group was carried out according to ASTM D 2073. More specifically, about 10 g of a sample (radical-reactive organopolysiloxane) was weighed and sampled in a flask, and 50 mL of ethanol was added thereto, followed by stirring the contents of the flask. Using a potentiometric titration apparatus, the resulting reaction solution was subjected to titration with a 0.2 mol/L ethanolic hydrochloric acid solution. At the same time, a blank test of the above measurement was conducted to correct the above measured value.

From the amount of the amino group thus measured, a conversion rate a (%) of the amino group was first determined from the following formula (II):

$$\alpha(\%)=[1-[a_1\times(f+g)/(a_0\times f)]]\times 100 \quad \text{(II)}.$$

In the above formula (II), $a_0$ and $a_1$ are the number of moles of the amino group per a unit mass of the side-chain primary aminopropyl-modified organopolysiloxane and the number of moles of the amino group per a unit mass of a reaction mixture obtained after the reaction thereof with the radical reactivity-imparting agent, respectively; f is a total amount of the side-chain primary aminopropyl-modified organopolysiloxane charged; and g is a total amount of the radical reactivity-imparting agent charged.

Assuming that the radical-reactive organopolysiloxane obtained after the reaction had the same number of sulfanyl groups produced thereon as that of amino groups consumed by the reaction, the number of moles (S) of the sulfanyl group per a unit mass of the sulfanyl group-modified organopolysiloxane was calculated from the following calculation formula (III):

$$S\ (\text{mol/g})=(a_0\times f\times \alpha/100)/[f+(a_0\times f\times \alpha/100)\times h] \quad \text{(III)}.$$

In the above formula (III), $a_0$, $a_1$, f and g are the same as $a_0$, $a_1$, f and g as defined the above formula (II); and h is a molecular weight of the radical reactivity-imparting agent.

<Method of Measuring Conversion Rate of Unsaturated Monomers>

The conversion rate of the respective unsaturated monomers upon the polymerization reaction was determined as follows. That is, the amounts of the unreacted unsaturated monomers were measured by gas chromatography under the following conditions to calculate a conversion rate thereof.

[Measuring Conditions of Gas Chromatography]
Column: "SUPELCO PTA-5" (available from Sigma-Aldrich; 30 m×250 μm×0.5 μm)
Mode: Splitless mode
Injection inlet temperature: 250° C.
Oven: 40 to 280° C.
Detector: FID
Detector temperature: 300° C.
Sample: 50 mg/g ethanol solution; 1.0 μL Synthesis Example 1

Synthesis of Radical-Reactive Organopolysiloxane A

A separable flask equipped with a reflux condenser, a thermometer, a nitrogen inlet tube and a stirrer was charged with 100 g of a side-chain primary aminopropyl-modified organopolysiloxane "KF-8003" (weight-average molecular weight: 50,000; number of moles of an amino group per a unit mass thereof: 1/1,970 mol/g; available from Shin-Etsu Chemical Co., Ltd.) as a reactive functional group-containing organopolysiloxane and 8 g of N-acetyl-DL-homocysteine thiolactone. The contents of the flask were heated to 100° C. and stirred for 3 h in a nitrogen atmosphere, thereby synthesizing a sulfanyl group-containing radical-reactive organopolysiloxane Si—SH A. As a result of subjecting the resulting reaction solution to potentiometric titration measurement to determine a residual amount of an amino group remaining in the reaction solution, it was confirmed that 98% of the amino group of the side-chain primary aminopropyl-modified organopolysiloxane as the raw material was reacted with N-acetyl-DL-homocysteine thiolactone (conversion rate of amino group: 98%). Therefore, the number of moles of the sulfanyl group per a unit mass of the radical-reactive organopolysiloxane Si—SH A was 1/2,170 mol/g. As a result of subjecting the radical-reactive organopolysiloxane A to GPC measurement, it was confirmed that the radical-reactive organopolysiloxane Si—SH A had a weight-average molecular weight of 50,000.

Synthesis Example 2

The procedure was carried out in the same manner as in Synthesis Example 1 except that the side-chain primary aminopropyl-modified organopolysiloxane was replaced with the organopolysiloxane (available from Dow Corning Toray Co., Ltd.) having the number of moles of an amino group per a unit mass thereof and a weight-average molecular weight as shown in Table 1, thereby obtaining a radical-reactive organopolysiloxane Si—SH B.

TABLE 1

| | | Synthesis Example 1 | Synthesis Example 2 |
|---|---|---|---|
| Side-chain primary aminopropyl-modified organopolysiloxane | Weight-average molecular weight | 50,000 | 30,000 |
| | Number of moles of amino group (mol/g)*[1] | 1/1,970 | 1/2,030 |
| Conversion rate of amino group by reaction (%) | | 98 | 99 |
| Radical-reactive organopolysiloxane | Name | Si—SH A | Si—SH B |
| | Weight-average molecular weight | 50,000 | 30,000 |
| | Number of moles of sulfanyl group (mol/g)*[2] | 1/2,170 | 1/2,210 |

Note
*[1] Per a unit mass of the side-chain primary aminopropyl-modified organopolysiloxane
*[2] Per a unit mass of the radical-reactive organopolysiloxane Example 1

Synthesis of Organopolysiloxane Graft Polymer A

A separable flask equipped with a reflux condenser, a thermometer, a nitrogen inlet tube and a stirrer was charged with 20 g of ethanol. While stirring contents of the flask at a refluxing temperature of ethanol under normal pressures in a nitrogen atmosphere, the following solutions (a) and (b) were respectively charged in separate dropping funnels and added dropwise at the same time to the flask over 3 h.

Solution (a): Solution prepared by mixing 14.7 g of N-[(dimethylamino)propyl]acrylamide (available from Wako Pure Chemical Industries, Ltd.; hereinafter referred to as "DMAPAA"), 9.8 g of N-tert-butyl acrylamide (available from Wako Pure Chemical Industries, Ltd.; hereinafter referred to as "t-BuAAm") and 45.6 g of ethanol.

Solution (b): Solution prepared by mixing 30 g of the radical-reactive organopolysiloxane Si—SH A synthesized in the above Synthesis Example 1, 0.3 g of 2,2'-azobis(2,4-dimethyl valeronitrile) (available from Wako Pure Chemical Industries, Ltd.; azo-based polymerization initiator; tradename: "V-65B") and 16.2 g of ethanol.

After completion of the dropwise addition, the reaction solution was stirred for 1 h while refluxing ethanol therethrough. At this time, the polymerization was substantially terminated. As a result of measuring conversion rates of DMAPAA and tBuAAm in the reaction solution, it was confirmed that conversion rates of DMAPAA and tBuAAm therein were 87% and 86%, respectively. Thereafter, in order to reduce an amount of the respective unreacted unsaturated monomers, the following solution (c) was added dropwise to the reaction solution over 1 h.

Solution (c): Solution prepared by mixing 0.3 g of 2,2'-azobis(2,4-dimethyl valeronitrile) (available from Wako Pure Chemical Industries, Ltd.; azo-based polymerization initiator; tradename: "V-65B") and 10 g of ethanol.

After completion of the dropwise addition, the reaction solution was stirred for 1 h while refluxing ethanol therethrough, and then conversion rates of DMAPAA and tBuAAm therein were measured. As a result, it was confirmed that conversion rates of DMAPAA and tBuAAm in the reaction solution were 95% and 94%, respectively. The reaction solution was allowed to stand and cooled to room temperature, and 8.5 g of lactic acid (available from Wako Pure Chemical Industries, Ltd.) as a neutralizing agent was added thereto. The solvent was removed from the reaction mixture under reduced pressure, thereby obtaining an organopolysiloxane graft polymer A as a light yellow solid.

Examples 2 to 11

Synthesis of Organopolysiloxane Graft Polymers B to K

The same procedure as in Example 1 was repeated except that kinds and charging amounts of the radical-reactive organopolysiloxane, nonionic unsaturated monomer having Tg of 60° C. or higher and cationic unsaturated monomer used as well as an amount of the neutralizing agent added were varied as shown in Table 2, thereby obtaining organopolysiloxane graft polymers B to K in the form of a solid.

TABLE 2

| | Examples | | | | | | | | | | |
|---|---|---|---|---|---|---|---|---|---|---|---|
| | 1 | 2 | 3 | 4 | 5 | 6 | 7 | 8 | 9 | 10 | 11 |
| Radical-reactive organopolysiloxane | | | | | | | | | | | |
| Si-SH A | | | | | | | | | | | |
| Amount charged (g) | 30.0 | 30.0 | 30.0 | — | 19.0 | 38.2 | 30.0 | 30.0 | 30.0 | 30.0 | 30.0 |
| Mass ratio charged[1] | 55% | 55% | 55% | — | 35% | 70% | 55% | 55% | 55% | 55% | 55% |
| Si-SH B | | | | | | | | | | | |
| Amount charged (g) | — | — | — | 30.0 | — | — | — | — | — | — | — |
| Mass ratio charged[1] | — | — | — | 55% | — | — | — | — | — | — | — |
| Nonionic unsaturated monomer having Tg of 60° C. or higher | | | | | | | | | | | |
| tBuAAm | | | | | | | | | | | |
| Amount charged (g) | 9.8 | 16.0 | 22.1 | 16.0 | 22.9 | 10.6 | — | 16.0 | — | 12.3 | 17.2 |
| Mass ratio charged[2] | 40% | 65% | 90% | 65% | 65% | 65% | — | 65% | — | 50% | 70% |
| tBuMA | | | | | | | | | | | |
| Amount charged (g) | — | — | — | — | — | — | 16.0 | — | 16.0 | — | — |
| Mass ratio charged[2] | — | — | — | — | — | — | 65% | — | 65% | — | — |
| Cationic unsaturated monomer | | | | | | | | | | | |
| DMAPAA | | | | | | | | | | | |
| Amount charged (g) | 14.7 | 8.6 | 2.5 | 8.6 | 12.4 | 5.7 | 8.6 | — | — | 6.1 | 3.7 |
| Mass ratio charged[2] | 60% | 35% | 10% | 35% | 35% | 35% | 35% | — | — | 25% | 15% |
| DEAEMA | | | | | | | | | | | |
| Amount charged (g) | — | — | — | — | — | — | — | 8.6 | 8.6 | — | — |
| Mass ratio charged[2] | — | — | — | — | — | — | — | 35% | 35% | — | — |
| Other unsaturated monomer | | | | | | | | | | | |
| HEAAm | | | | | | | | | | | |
| Amount charged (g) | — | — | — | — | — | — | — | — | — | 6.1 | — |
| Mass ratio charged[2] | — | — | — | — | — | — | — | — | — | 25% | — |
| PEGMA | | | | | | | | | | | |
| Amount charged (g) | — | — | — | — | — | — | — | — | — | — | 3.7 |
| Mass ratio charged[2] | — | — | — | — | — | — | — | — | — | — | 15% |
| Neutralizing agent | | | | | | | | | | | |
| Lactic acid | | | | | | | | | | | |
| Amount added (g) | 8.5 | 5.0 | 1.4 | 5.0 | 7.1 | 3.3 | 5.0 | 4.2 | 4.2 | 3.5 | 2.1 |
| Organopolysiloxane graft polymer | A | B | C | D | E | F | G | H | I | J | K |

Note
[1]Content of a radical-reactive organopolysiloxane based on a total amount of the radical-reactive organopolysiloxane and unsaturated monomers charged.
[2]Content of respective unsaturated monomers based on a total amount of the unsaturated monomers charged.

Comparative Examples 1 to 4

Synthesis of Organopolysiloxane Graft Polymers L to O

The same procedure as in Example 1 was repeated except that kinds and charging amounts of the radical-reactive organopolysiloxane, nonionic unsaturated monomer having Tg of 60° C. or higher and cationic unsaturated monomer used were varied as shown in Table 3, thereby obtaining organopolysiloxane graft polymers L to O in the form of a solid.

TABLE 3

|  | Comparative Examples | | | |
| --- | --- | --- | --- | --- |
|  | 1 | 2 | 3 | 4 |
| Radical-reactive organopolysiloxane Si—SHA | | | | |
| Amount charged (g) | 21.8 | 30.0 | 16.4 | 40.9 |
| Mass ratio charged[1] | 40% | 55% | 30% | 75% |
| Nonionic unsaturated monomer having Tg of 60° C. or higher tBuAAm | | | | |
| Amount charged (g) | 31.065 | 8.1 | 24.9 | 8.9 |
| Mass ratio charged[2] | 95% | 33% | 65% | 65% |
| Cationic unsaturated monomer DMAPAA | | | | |
| Amount charged (g) | 1.6 | 8.1 | 13.4 | 4.8 |
| Mass ratio charged[2] | 5% | 33% | 35% | 35% |
| Other unsaturated monomer HEAAm | | | | |
| Amount charged (g) | — | 8.1 | — | — |
| Mass ratio charged[2] | — | 33% | — | — |
| Neutralizing agent Lactic acid | | | | |
| Amount added (g) | 0.9 | 4.1 | 7.7 | 2.8 |
| Organopolysiloxane graft polymer | L | M | N | O |

Note
[1] Content of a radical-reactive organopolysiloxane based on a total amount of the radical-reactive organopolysiloxane and unsaturated monomers charged.
[2] Content of respective unsaturated monomers based on a total amount of the unsaturated monomers charged.

Symbols shown in Tables 2 and 3 have the following meanings.

tBuMA: t-Butyl methacrylate (available from Wako Pure Chemical Industries, Ltd.)

DEAEMA: Diethylaminoethyl methacrylate (available from Wako Pure Chemical Industries, Ltd.)

HEAAm: N-(2-hydroxyethyl)acrylamide (available from Kohjin Co., Ltd.)

PEGMA: Methacrylic acid methoxy polyethylene glycol (average molar number of addition: 9) (available from Nippon Nyukazai Co., Ltd.)

[Evaluation]

<Evaluation of Hair Settability>

A 5% by mass ethanol solution of each of the organopolysiloxane graft polymers respectively obtained in Examples 1 to 11 and Comparative Examples 1 to 4 was prepared, and the thus prepared solution was applied onto hair to evaluate a hair settability thereof under the following conditions. The results are collectively shown in Table 4.

(Evaluation Conditions)

A hair bundle of Caucasian curly or kinky hair having a length of 30 cm and a weight of 6 g was used for the evaluation. The hair bundle was wetted with water to moisten a whole portion thereof, and 1.2 g of the 5% by mass ethanol solution of each of the organopolysiloxane graft polymers was applied thereonto, and then the hair bundle was combed alternately from front and back sides thereof 5 times on each side. Next, the hair bundle was completely dried using a dryer. Then, a root portion of the hair bundle was nipped by a straightening iron (available from CREATE Corp.; registered trademark: CREATE ION; 150 to 160° C.), and the straightening iron was slid over the hair bundle towards a tip end thereof to stretch the hair bundle, and the stretching treatment was repeated 3 times. Thereafter, the similar treatment was further repeated 2 times along with combing. After completing a series of the above treatments, the hair bundle was cooled to room temperature, and then evaluated by naked eyes according to the following ratings. The evaluation of each of the items was conducted 5 times in total by three expert panelists to obtain an average value thereof.

(Evaluation Criteria)

(1) Finish of Hair Style

Under the above treating conditions for the hair bundle, the condition of the hair bundle after being cooled to room temperature was observed by naked eyes and evaluated according the following ratings. When the average evaluation score was 4.0 or more, the finish of hair style was regarded as being good.

5: Curl or kink of hair was stretched straight, and an entire portion of the hair bundle was collected like one plate.

4: Curl or kink of hair was stretched straight, and substantially an entire portion of the hair bundle was collected together.

3: Curl or kink of hair was stretched, but the hair bundle was collected weakly.

2: Curl or kink of hair was stretched, but the hair bundle was not collected at all.

1: Curl or kink of hair was not stretched.

(2) Hair Set Retentivity Under High Humidity Conditions

The hair bundle after completing a series of the treatments under the above hair treating conditions was suspended such that hair tips thereof faced downwards, and allowed to stand in this state under environmental conditions of a temperature of 25° C. and a relative humidity of 90% or more. After allowing the hair bundle to stand under the above conditions for 1 h, the condition of the hair bundle was observed and evaluated by naked eyes. When the average evaluation score was 3.0 or more, the hair set retentivity under high humidity conditions was regarded as being good.

5: Curl or kink of the hair was kept in a stretched state, and the hair bundle was kept in a collected state as a whole.

4: Curl or kink of the hair was kept substantially in a stretched state, but a tip end of the hair bundle was collected only weakly.

3: An entire portion of the hair suffered from undulation, and the hair bundle was collected weakly.

2: The hair suffered from remarkable undulation, and the hair bundle was collected weakly.

1: The hair bundle was dispersed as a whole.

TABLE 4

| | Examples | | | | | | | | | | | Comparative Examples | | | |
|---|---|---|---|---|---|---|---|---|---|---|---|---|---|---|---|
| | 1 | 2 | 3 | 4 | 5 | 6 | 7 | 8 | 9 | 10 | 11 | 1 | 2 | 3 | 4 |
| Organopolysiloxane graft polymer | A | B | C | D | E | F | G | H | I | J | K | L | M | N | O |
| Hair settability | | | | | | | | | | | | | | | |
| Finish of hair style | 4.6 | 5.0 | 4.8 | 5.0 | 5.0 | 4.0 | 4.8 | 4.8 | 4.4 | 4.4 | 4.6 | 3.4 | 3.2 | 3.2 | 3.4 |
| Hair set retentivity under high humidity conditions | 3.8 | 5.0 | 5.0 | 5.0 | 3.4 | 3.2 | 4.8 | 4.6 | 4.2 | 3.8 | 3.6 | 3.2 | 1.4 | 2.4 | 2.2 |

INDUSTRIAL APPLICABILITY

The organopolysiloxane graft polymer according to the present invention is optimum for use in a hairdressing method in which a hair is shaped at a hair temperature of 50° C. or higher, and then cooled to a temperature of lower than 50° C. to fix a style of the hair thus shaped, and is excellent in hair set retentivity under high humidity conditions and therefore can be effectively used as a hair cosmetic.

The invention claimed is:

1. A method of applying an organopolysiloxane graft polymer to hair, wherein the organopolysiloxane graft polymer comprises an organopolysiloxane segment as a main chain thereof and an unsaturated monomer-derived polymer segment as a side chain thereof, in which a content of the organopolysiloxane segment in the organopolysiloxane graft polymer is not less than 35% by mass and not more than 70% by mass, and the unsaturated monomer-derived polymer segment contains a repeating unit derived from a nonionic unsaturated monomer having a glass transition temperature Tg of 60° C. or higher (except for a repeating unit derived from an unsaturated monomer containing an amino group) in an amount of not less than 40% by mass and not more than 90% by mass, and further contains a repeating unit derived from a cationic unsaturated monomer in an amount of not less than 10% by mass and not more than 60% by mass.

2. The method of applying the organopolysiloxane graft polymer to hair according to claim 1, wherein the organopolysiloxane segment has a weight-average molecular weight of not less than 5,000 and not more than 200,000.

3. The method of applying the organopolysiloxane graft polymer to hair according to claim 1, wherein the organopolysiloxane segment has a molecular weight between graft points of not less than 500 and not more than 20,000.

4. The method of applying the organopolysiloxane graft polymer to hair according to claim 1, wherein the repeating unit derived from the nonionic unsaturated monomer comprises a repeating unit derived from at least one unsaturated monomer selected from the group consisting of tert-butyl acrylate, acrylamide, N-sec-butyl acrylamide, N-tert-butyl acrylamide, N,N-dibutyl acrylamide, N,N-diisopropyl acrylamide, N,N-dimethyl acrylamide, isohexyl acrylamide, isooctyl acrylamide, N-(1-methylbutyl)acrylamide, sec-butyl methacrylate, tert-butyl methacrylate and N-tert-butyl methacrylamide.

5. The method of applying the organopolysiloxane graft polymer to hair according to claim 1, wherein the repeating unit derived from the cationic unsaturated monomer is a repeating unit derived from a compound represented by the general formula (3):

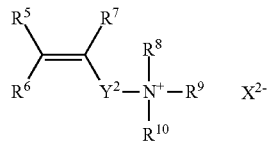

(3)

wherein $R^5$, $R^6$ and $R^7$ are each independently a hydrogen atom or a methyl group; $R^8$, $R^9$ and $R^{10}$ are each independently a hydrogen atom or an alkyl group having 1 to 3 carbon atoms; $Y^2$ is a group selected from the group consisting of an alkylene group having 1 to 12 carbon atoms, $-COOR^{11}-$, $-CONHR^{11}-$, $-OCOR^{11}-$ and $-R^{12}-OCO-R^{11}-$ wherein $R^{11}$ and $R^{12}$ are each independently an alkylene group having 1 to 5 carbon atoms; and $X^{2-}$ is an anion.

6. The method of applying the organopolysiloxane graft polymer to hair according to claim 1, wherein a total content of the repeating unit derived from the nonionic unsaturated monomer having a glass transition temperature Tg of 60° C. or higher and the repeating unit derived from the cationic unsaturated monomer in the unsaturated monomer-derived polymer segment is not less than 90% by mass and not more than 100% by mass.

7. The method of applying the organopolysiloxane graft polymer to hair according to claim 1, wherein the organopolysiloxane graft polymer is obtained by polymerizing unsaturated monomers containing the nonionic unsaturated monomer having a glass transition temperature Tg of 60° C. or higher and the cationic unsaturated monomer in the presence of a radical-reactive organopolysiloxane represented by the general formula (5) or (6):

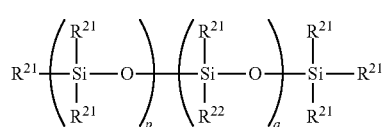

(5)

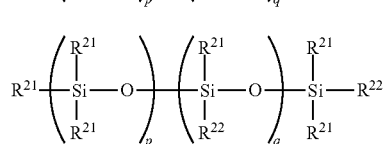

(6)

wherein $R^{21}$ groups are each independently an alkyl group having not less than 1 and not more than 22 carbon atoms or an aryl group having not less than 6 and not more than 14 carbon atoms; $R^{22}$ is an alkyl group containing a radical-reactive functional group; p is a number of not less than 2 and not more than 4000; and q is a number of not less than 2 and not more than 500, in which repeating units in number of p and repeating units in number of q may be bonded to each other either in a block form or in a random form.

8. The method of applying the organopolysiloxane graft polymer to hair according to claim 7, wherein the radical-reactive functional group is selected from the group consisting of an ethylenically unsaturated group, a halogeno group and a sulfanyl group.

9. The method of applying the organopolysiloxane graft polymer to hair according to claim 7, wherein the radical-reactive organopolysiloxane is obtained by reacting an organopolysiloxane containing a reactive functional group represented by the general formula (7) or (8) with a radical reactivity-imparting agent:

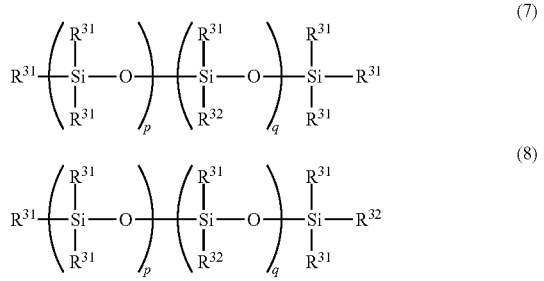

wherein $R^{31}$ groups are each independently an alkyl group having 1 to 22 carbon atoms or an aryl group having 6 to 14 carbon atoms; $R^{32}$ is an alkyl group containing a reactive functional group; p is a number of not less than 2 and not more than 4,000; and q is a number of not less than 2 and not more than 500, in which repeating units in number of p and repeating units in number of q may be bonded to each other either in a block form or in a random form.

10. The method of applying the organopolysiloxane graft polymer to hair according to claim 7, wherein the reactive functional group is selected from the group consisting of a hydroxy group, an amino group, a carboxy group and an epoxy group.

11. A process for producing a hair cosmetic comprising an organopolysiloxane graft polymer comprising an organopolysiloxane segment as a main chain thereof and an unsaturated monomer-derived polymer segment as a side chain thereof, said process comprising the step of polymerizing unsaturated monomers containing a nonionic unsaturated monomer having a glass transition temperature Tg of 60° C. or higher and a cationic unsaturated monomer in the presence of a radical-reactive organopolysiloxane represented by the general formula (5) or (6):

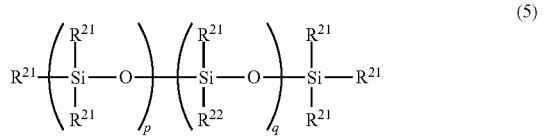

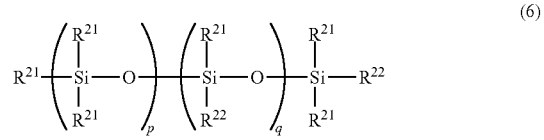

wherein $R^{21}$ groups are each independently an alkyl group having not less than 1 and not more than 22 carbon atoms or an aryl group having not less than 6 and not more than 14 carbon atoms; $R^{22}$ is an alkyl group containing a radical-reactive functional group; p is a number of not less than 2 and not more than 4,000; and q is a number of not less than 2 and not more than 500, in which repeating units in number of p and repeating units in number of q may be bonded to each other either in a block form or in a random form, in which a content of the organopolysiloxane segment in the resulting organopolysiloxane graft polymer is not less than 35% by mass and not more than 70% by mass, and the unsaturated monomer-derived polymer segment contains a repeating unit derived from the nonionic unsaturated monomer having a glass transition temperature Tg of 0.60° C. or higher (except for a repeating unit derived from an unsaturated monomer containing an amino group) in an amount of not less than 40% by mass and not more than 90% by mass, and further contains a repeating unit derived from the cationic unsaturated monomer in an amount of not less than 10% by mass and not more than 60% by mass.

12. The process for producing the hair cosmetic comprising the organopolysiloxane graft polymer according to claim 11, wherein the radical-reactive functional group is selected from the group consisting of an ethylenically unsaturated group, a halogeno group and a sulfanyl group.

13. The process for producing the hair cosmetic comprising the organopolysiloxane graft polymer according to claim 11, wherein number of carbon atoms of the alkyl group containing a radical-reactive functional group which is represented by $R^{22}$ in the general formula (5) and (6) is not less than 2 and not more than 20.

14. The process for producing the hair cosmetic comprising the organopolysiloxane graft polymer according to claim 11, wherein the radical-reactive organopolysiloxane has a weight-average molecular weight of not less than 5,000 and not more than 200,000.

15. The process for producing the hair cosmetic comprising the organopolysiloxane graft polymer according to claim 11, wherein the radical-reactive functional group is present in an amount of not less than 1/10,000 mol/g and not more than 1/500 mol/g per a unit mass of the radical-reactive organopolysiloxane.

16. The process for producing the hair cosmetic comprising the organopolysiloxane graft polymer according to claim 11, wherein a total content of the nonionic unsaturated monomer having a glass transition temperature Tg of 60° C. or higher and the cationic unsaturated monomer in the unsaturated monomers is not less than 90% by mass and not more than 100% by mass.

17. The process for producing the hair cosmetic comprising the organopolysiloxane graft polymer according to claim 11, wherein the radical-reactive organopolysiloxane is obtained by reacting an organopolysiloxane containing a reactive functional group represented by the general formula (7) or (8) with a radical reactivity-imparting agent:

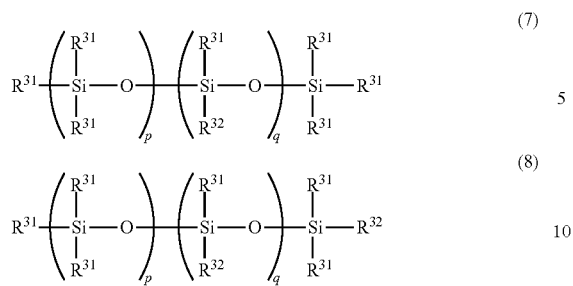

(7)

(8)

wherein $R^{31}$ groups are each independently an alkyl group having 1 to 22 carbon atoms or an aryl group having 6 to 14 carbon atoms; $R^{32}$ is an alkyl group containing a reactive functional group; p is a number of not less than 2 and not more than 4,000; and q is a number of not less than 2 and not more than 500, in which repeating units in number of p and repeating units in number of q may be bonded to each other either in a block form or in a random form.

18. The process for producing the hair cosmetic comprising the organopolysiloxane graft polymer according to claim 11, wherein the reactive functional group is selected from the group consisting of a hydroxy group, an amino group, a carboxy group and an epoxy group.

\* \* \* \* \*